US010660698B2

(12) United States Patent
Willard et al.

(10) Patent No.: US 10,660,698 B2
(45) Date of Patent: May 26, 2020

(54) DEVICES AND METHODS FOR NERVE MODULATION

(71) Applicant: Boston Scientific Scimed, Inc., Maple Grove, MN (US)

(72) Inventors: Martin R. Willard, Burnsville, MN (US); Patrick A. Haverkost, Brooklyn Center, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1235 days.

(21) Appl. No.: 14/327,154

(22) Filed: Jul. 9, 2014

(65) Prior Publication Data

US 2015/0018818 A1    Jan. 15, 2015

Related U.S. Application Data

(60) Provisional application No. 61/845,289, filed on Jul. 11, 2013.

(51) Int. Cl.
| A61B 18/14 | (2006.01) |
| A61M 25/10 | (2013.01) |
| A61N 1/36 | (2006.01) |
| A61B 18/00 | (2006.01) |
| A61M 25/06 | (2006.01) |

(52) U.S. Cl.
CPC ......... *A61B 18/1492* (2013.01); *A61M 25/10* (2013.01); *A61N 1/3606* (2013.01); *A61B 2018/00101* (2013.01); *A61B 2018/00267* (2013.01); *A61B 2018/00404* (2013.01); *A61B 2018/00434* (2013.01); *A61B 2018/00511* (2013.01); *A61B 2018/00791* (2013.01); *A61B 2018/00797* (2013.01); *A61B 2018/00821* (2013.01); *A61M 2025/0681* (2013.01)

(58) Field of Classification Search
CPC .. A61B 2018/00267; A61B 2018/0025; A61B 2018/00273; A61B 2018/00434; A61B 2018/00255
See application file for complete search history.

(56) References Cited

U.S. PATENT DOCUMENTS

| 164,184 A | 6/1875 | Kiddee |
| 852,787 A | 5/1907 | Hoerner |
| 921,973 A | 5/1909 | Gillett et al. |
| (Continued) | | |

FOREIGN PATENT DOCUMENTS

| DE | 10038737 A1 | 2/2002 |
| EP | 1053720 A1 | 11/2000 |
| (Continued) | | |

OTHER PUBLICATIONS

US 8,398,630 B2, 03/2013, Demarais et al. (withdrawn)
(Continued)

*Primary Examiner* — Michael F Peffley
*Assistant Examiner* — Bo Ouyang

(57) ABSTRACT

Systems for nerve and tissue modulation are disclosed. An illustrative system may include an intravascular nerve modulation system including a catheter shaft, an expandable basket and one or more electrode assemblies affixed to the expandable basket. The one or more electrode assemblies may be affixed to the expandable basket using one or more covers or coatings.

20 Claims, 13 Drawing Sheets

(56) References Cited

U.S. PATENT DOCUMENTS

| | | | |
|---|---|---|---|
| 976,733 A | 11/1910 | Gilliland |
| 1,167,014 A | 1/1916 | O'Brien |
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,531,943 A | 7/1985 | Van Tassel et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,890,623 A | 1/1990 | Cook et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A * | 10/1993 | Imran ............... A61B 5/0422 600/375 |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,290,306 A | 3/1994 | Trotta et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,512,051 A | 4/1996 | Wang et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,613,979 A | 3/1997 | Trotta et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |

(56) References Cited

U.S. PATENT DOCUMENTS

| | | |
|---|---|---|
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,687,737 A | 11/1997 | Branham et al. |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,807,306 A | 9/1998 | Shapland et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,091,995 A | 7/2000 | Ingle et al. |

(56) References Cited

U.S. PATENT DOCUMENTS

| | | | |
|---|---|---|---|
| 6,093,166 A | 7/2000 | Knudson et al. | |
| 6,096,021 A | 8/2000 | Helm et al. | |
| 6,099,526 A | 8/2000 | Whayne et al. | |
| 6,102,908 A | 8/2000 | Tu et al. | |
| 6,106,477 A | 8/2000 | Miesel et al. | |
| 6,110,187 A | 8/2000 | Donlon et al. | |
| 6,110,192 A | 8/2000 | Ravenscroft et al. | |
| 6,114,311 A | 9/2000 | Parmacek et al. | |
| 6,117,101 A | 9/2000 | Diederich et al. | |
| 6,117,128 A | 9/2000 | Gregory | |
| 6,120,476 A | 9/2000 | Fung et al. | |
| 6,120,516 A | 9/2000 | Selmon et al. | |
| 6,121,775 A | 9/2000 | Pearlman | |
| 6,123,679 A | 9/2000 | Lafaut et al. | |
| 6,123,682 A | 9/2000 | Knudson et al. | |
| 6,123,702 A | 9/2000 | Swanson et al. | |
| 6,123,703 A | 9/2000 | Tu et al. | |
| 6,123,718 A | 9/2000 | Tu et al. | |
| 6,129,725 A | 10/2000 | Tu et al. | |
| 6,135,997 A | 10/2000 | Laufer et al. | |
| 6,142,991 A | 11/2000 | Schatzberger et al. | |
| 6,142,993 A * | 11/2000 | Whayne | A61B 18/1492 600/374 |
| 6,149,647 A | 11/2000 | Tu et al. | |
| 6,152,899 A | 11/2000 | Farley et al. | |
| 6,152,912 A | 11/2000 | Jansen et al. | |
| 6,156,046 A | 12/2000 | Passafaro et al. | |
| 6,158,250 A | 12/2000 | Tibbals et al. | |
| 6,159,187 A | 12/2000 | Park et al. | |
| 6,159,225 A | 12/2000 | Makower | |
| 6,161,048 A | 12/2000 | Sluijter et al. | |
| 6,162,184 A | 12/2000 | Swanson et al. | |
| 6,165,163 A | 12/2000 | Chien et al. | |
| 6,165,172 A | 12/2000 | Farley et al. | |
| 6,165,187 A | 12/2000 | Reger et al. | |
| 6,168,594 B1 | 1/2001 | Lafontaine et al. | |
| 6,171,321 B1 | 1/2001 | Gifford, III et al. | |
| 6,179,832 B1 | 1/2001 | Jones et al. | |
| 6,179,835 B1 | 1/2001 | Panescu et al. | |
| 6,179,859 B1 | 1/2001 | Bates et al. | |
| 6,183,468 B1 | 2/2001 | Swanson et al. | |
| 6,183,486 B1 | 2/2001 | Snow et al. | |
| 6,190,379 B1 | 2/2001 | Heuser et al. | |
| 6,191,862 B1 | 2/2001 | Swanson et al. | |
| 6,197,021 B1 | 3/2001 | Panescu et al. | |
| 6,200,266 B1 | 3/2001 | Shokrollahi et al. | |
| 6,203,537 B1 | 3/2001 | Adrian | |
| 6,203,561 B1 | 3/2001 | Ramee et al. | |
| 6,210,406 B1 | 4/2001 | Webster | |
| 6,211,247 B1 | 4/2001 | Goodman | |
| 6,217,576 B1 | 4/2001 | Tu et al. | |
| 6,219,577 B1 | 4/2001 | Brown, III et al. | |
| 6,228,076 B1 | 5/2001 | Winston et al. | |
| 6,228,109 B1 | 5/2001 | Tu et al. | |
| 6,231,516 B1 | 5/2001 | Keilman et al. | |
| 6,231,587 B1 | 5/2001 | Makower | |
| 6,235,044 B1 | 5/2001 | Root et al. | |
| 6,236,883 B1 | 5/2001 | Ciaccio et al. | |
| 6,237,605 B1 | 5/2001 | Vaska et al. | |
| 6,238,389 B1 | 5/2001 | Paddock et al. | |
| 6,238,392 B1 | 5/2001 | Long | |
| 6,241,666 B1 | 6/2001 | Pomeranz et al. | |
| 6,241,753 B1 | 6/2001 | Knowlton | |
| 6,245,020 B1 | 6/2001 | Moore et al. | |
| 6,245,045 B1 | 6/2001 | Stratienko | |
| 6,248,126 B1 | 6/2001 | Lesser et al. | |
| 6,251,109 B1 * | 6/2001 | Hassett | A61B 18/1492 606/45 |
| 6,251,128 B1 | 6/2001 | Knopp et al. | |
| 6,258,087 B1 | 7/2001 | Edwards et al. | |
| 6,273,886 B1 | 8/2001 | Edwards et al. | |
| 6,280,466 B1 | 8/2001 | Kugler et al. | |
| 6,283,935 B1 | 9/2001 | Laufer et al. | |
| 6,283,959 B1 | 9/2001 | Lalonde et al. | |
| 6,284,743 B1 | 9/2001 | Parmacek et al. | |
| 6,287,323 B1 | 9/2001 | Hammerslag | |
| 6,290,696 B1 | 9/2001 | Lafontaine | |
| 6,292,695 B1 | 9/2001 | Webster, Jr. et al. | |
| 6,293,942 B1 | 9/2001 | Goble et al. | |
| 6,293,943 B1 | 9/2001 | Panescu et al. | |
| 6,296,619 B1 | 10/2001 | Brisken et al. | |
| 6,298,256 B1 | 10/2001 | Meyer | |
| 6,299,379 B1 | 10/2001 | Lewis | |
| 6,299,623 B1 | 10/2001 | Wulfman | |
| 6,309,379 B1 | 10/2001 | Willard et al. | |
| 6,309,399 B1 | 10/2001 | Barbut et al. | |
| 6,311,090 B1 | 10/2001 | Knowlton | |
| 6,317,615 B1 | 11/2001 | KenKnight et al. | |
| 6,319,242 B1 | 11/2001 | Patterson et al. | |
| 6,319,251 B1 | 11/2001 | Tu et al. | |
| 6,322,559 B1 | 11/2001 | Daulton et al. | |
| 6,325,797 B1 | 12/2001 | Stewart et al. | |
| 6,325,799 B1 | 12/2001 | Goble | |
| 6,328,699 B1 | 12/2001 | Eigler et al. | |
| 6,346,074 B1 | 2/2002 | Roth | |
| 6,346,104 B2 | 2/2002 | Daly et al. | |
| 6,350,248 B1 | 2/2002 | Knudson et al. | |
| 6,350,276 B1 | 2/2002 | Knowlton | |
| 6,353,751 B1 | 3/2002 | Swanson et al. | |
| 6,355,029 B1 | 3/2002 | Joye et al. | |
| 6,357,447 B1 | 3/2002 | Swanson et al. | |
| 6,361,519 B1 | 3/2002 | Knudson et al. | |
| 6,364,840 B1 | 4/2002 | Crowley | |
| 6,371,965 B2 | 4/2002 | Gifford, III et al. | |
| 6,375,668 B1 | 4/2002 | Gifford et al. | |
| 6,377,854 B1 | 4/2002 | Knowlton | |
| 6,377,855 B1 | 4/2002 | Knowlton | |
| 6,379,352 B1 | 4/2002 | Reynolds et al. | |
| 6,379,373 B1 | 4/2002 | Sawhney et al. | |
| 6,381,497 B1 | 4/2002 | Knowlton | |
| 6,381,498 B1 | 4/2002 | Knowlton | |
| 6,383,151 B1 | 5/2002 | Diederich et al. | |
| 6,387,105 B1 | 5/2002 | Gifford, III et al. | |
| 6,387,380 B1 | 5/2002 | Knowlton | |
| 6,389,311 B1 | 5/2002 | Whayne et al. | |
| 6,389,314 B2 | 5/2002 | Feiring | |
| 6,391,024 B1 | 5/2002 | Sun et al. | |
| 6,394,096 B1 | 5/2002 | Constantz | |
| 6,394,956 B1 | 5/2002 | Chandrasekaran et al. | |
| 6,398,780 B1 | 6/2002 | Farley et al. | |
| 6,398,782 B1 | 6/2002 | Pecor et al. | |
| 6,398,792 B1 | 6/2002 | O'Connor | |
| 6,401,720 B1 | 6/2002 | Stevens et al. | |
| 6,402,719 B1 | 6/2002 | Ponzi et al. | |
| 6,405,090 B1 | 6/2002 | Knowlton | |
| 6,409,723 B1 | 6/2002 | Edwards | |
| 6,413,255 B1 | 7/2002 | Stern | |
| 6,421,559 B1 | 7/2002 | Pearlman | |
| 6,423,057 B1 | 7/2002 | He et al. | |
| 6,425,867 B1 | 7/2002 | Vaezy et al. | |
| 6,425,912 B1 | 7/2002 | Knowlton | |
| 6,427,118 B1 | 7/2002 | Suzuki | |
| 6,428,534 B1 | 8/2002 | Joye et al. | |
| 6,428,536 B2 | 8/2002 | Panescu et al. | |
| 6,430,446 B1 | 8/2002 | Knowlton | |
| 6,432,102 B2 | 8/2002 | Joye et al. | |
| 6,436,056 B1 | 8/2002 | Wang et al. | |
| 6,438,424 B1 | 8/2002 | Knowlton | |
| 6,440,125 B1 | 8/2002 | Rentrop | |
| 6,442,413 B1 | 8/2002 | Silver | |
| 6,443,965 B1 | 9/2002 | Gifford, III et al. | |
| 6,445,939 B1 | 9/2002 | Swanson et al. | |
| 6,447,505 B2 | 9/2002 | McGovern et al. | |
| 6,447,509 B1 | 9/2002 | Bonnet et al. | |
| 6,451,034 B1 | 9/2002 | Gifford, III et al. | |
| 6,451,044 B1 | 9/2002 | Naghavi et al. | |
| 6,453,202 B1 | 9/2002 | Knowlton | |
| 6,454,737 B1 | 9/2002 | Nita et al. | |
| 6,454,757 B1 | 9/2002 | Nita et al. | |
| 6,454,775 B1 | 9/2002 | Demarais et al. | |
| 6,458,098 B1 | 10/2002 | Kanesaka | |
| 6,461,378 B1 | 10/2002 | Knowlton | |
| 6,468,276 B1 | 10/2002 | McKay | |
| 6,468,297 B1 | 10/2002 | Williams et al. | |

(56) References Cited

U.S. PATENT DOCUMENTS

| | | |
|---|---|---|
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung |
| 6,602,246 B1 | 8/2003 | Joye et al. |
| 6,605,056 B2 | 8/2003 | Eidenschink et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B2 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |

(56) References Cited

U.S. PATENT DOCUMENTS

| | | |
|---|---|---|
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,923,808 B2 | 8/2005 | Taimisto |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |

(56) References Cited

U.S. PATENT DOCUMENTS

| | | |
|---|---|---|
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,480 B2 | 1/2008 | Eidenschink et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,686,841 B2 | 3/2010 | Eidenschink et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |

(56) References Cited

U.S. PATENT DOCUMENTS

| | | |
|---|---|---|
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,043,673 B2 | 10/2011 | Lee et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,168,275 B2 | 5/2012 | Lee et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |

(56) References Cited

U.S. PATENT DOCUMENTS

| | | |
|---|---|---|
| 2003/0050635 A1 | 3/2003 | Truckai et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0229340 A1 | 12/2003 | Sherry et al. |
| 2003/0233099 A1 | 12/2003 | Danaek et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0096647 A1 | 5/2005 | Steinke et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0273149 A1 | 12/2005 | Tran et al. |
| 2005/0288730 A1 | 12/2005 | Deem et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0085054 A1 | 4/2006 | Zikorus et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0129143 A1* | 6/2006 | Flaxmeier .......... A61B 18/1492 606/29 |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0182873 A1 | 8/2006 | Klisch et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0067883 A1 | 3/2007 | Sretavan |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |

(56) References Cited

U.S. PATENT DOCUMENTS

| | | |
|---|---|---|
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1* | 7/2008 | Steinke .............. A61B 18/1492 606/41 |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |

(56) References Cited

U.S. PATENT DOCUMENTS

| | | |
|---|---|---|
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |
| 2014/0074083 A1 | 3/2014 | Horn et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 9935986 | 7/1999 |
| WO | 0047118 A1 | 8/2000 |
| WO | 0066021 | 11/2000 |
| WO | 0195820 | 12/2001 |
| WO | 03026525 A1 | 4/2003 |
| WO | 2004100813 A2 | 11/2004 |
| WO | 2004110258 A2 | 12/2004 |
| WO | 2005041810 | 5/2005 |
| WO | 2006105121 A2 | 10/2006 |
| WO | 2008014465 A2 | 1/2008 |
| WO | 2009121017 A1 | 10/2009 |
| WO | 2010067360 A2 | 6/2010 |

(56) References Cited

FOREIGN PATENT DOCUMENTS

| WO | 2010102310 A2 | 9/2010 |
|---|---|---|
| WO | 2010132703 | 11/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |
| WO | 2013086461 A1 | 6/2013 |

OTHER PUBLICATIONS

CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18, 2004.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572, Dec. 2004.
Baun, "Interaction with Soft Tissue," Principles of General & Vascular Sonography, Chapter 2, pp. 23-24, Before Mar. 2012.
Blue Cross Blue Shield Medical Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhou et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Products—Functional Measurement," Volcano Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-49, Nov. 6, 1997.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.

(56) References Cited

OTHER PUBLICATIONS

Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.

Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.

Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.

Popma et al., "Percutaneous Coronary and Valvular Intervention," Braunwald's Heart Disease: A Textbook of Cardiovascular Medicine, 7th edition, p. 1364-1405, 2005.

Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.

Romer et al., "Histopathology of Human Coronary Atherosclerosis by Quantifying Its Chemical Composition With Raman Spectroscopy," Circulation, 1998, p. 878-885, vol. 97.

Schauerte et al., "Catheter Ablation of Cardiac Autonomic Nerves for Prevention of Vagal Atrial Fibrillation," Circulation, 2000, p. 2774-2780, vol. 102.

Scheller et al., "Intracoronary Paclitaxel Added to Contrast Media Inhibits In-Stent Restenosis of Porcine Coronary Arteries," American Heart Association, 2002, p. 2227.

Scheller et al., "Potential solutions to the current problem: coated balloon," EuroIntervention, 2008, p. C63-C66, vol. 4 (Supplement C).

Shaffer, "Scientific basis of laser energy," Clinics in Sports Medicine, 2002, p. 585-598, vol. 21.

Shmatukha et al., "MRI temperature mapping during thermal balloon angioplasty," Physics in Medicine and Biology, 2006, p. N163-N171, vol. 51.

Slager et al., "Vaporization of Atherosclerotic Plaques by Spark Erosion," J Am Coll Cardiol, 1985, p. 21-25.

Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.

Suselbeck et al., "In vivo intravascular electric impedance spectroscopy using a new catheter with integrated microelectrodes," Basic Res Cardiol, 2005, p. 28-34, vol. 100.

Suselbeck et al., "Intravascular electric impedance spectroscopy of atherosclerotic lesions using a new impedance catheter system," Basic Res Cardiol, 2005, p. 446-452, vol. 100.

Tepe et al., "Local Delivery of Paclitaxel to Inhibit Restenosis during Angioplasty of the Leg," The New England Journal of Medicine, 2008, p. 689-699, vol. 358.

"Optical Coherence Tomography: Advantages of OCT," LightLab Imaging Technology, printed Sep. 3, 2003.

"Optical Coherence Tomography: Image Gallery Cardiovascular Procedures," LightLab Imaging Technology, printed Sep. 3, 2003.

"Optical Coherence Tomography: What is OCT?," LightLab Imaging Technology, printed Sep. 3, 2003.

"Optical Coherence Tomography: Why Use OCT?," LightLab Imaging Technology, printed Sep. 3, 2003.

Pieper et al. "Design and implementation of a new computerized system for intraoperative cardiac mapping", J. Appl. Physiol. 71(4): 1529-1539, 1991.

\* cited by examiner

DEVICES AND METHODS FOR NERVE MODULATION

CROSS-REFERENCE TO RELATED APPLICATIONS

This application claims priority under 35 U.S.C. § 119 to U.S. Provisional Application Ser. No. 61/845,289, filed Jul. 11, 2013, the entirety of which is incorporated herein by reference.

FIELD

The invention generally pertains to percutaneous and intravascular devices for nerve modulation and/or ablation.

BACKGROUND

Certain treatments involve, and in some cases require, the temporary or permanent interruption or modification of select nerve function. One example treatment is renal nerve ablation, which can be used to treat conditions related to congestive heart failure. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many body tissues, such as nerves, including renal nerves, brain tissue, cardiac tissue and the tissue of other body organs, are in close proximity to blood vessels and/or other body cavities. This proximity enables the tissues to be accessed percutaneously or intravascularly through walls of the blood vessels. In some instances, it may be desirable to ablate perivascular nerves using a radio frequency (RF) electrode. In other instances, the perivascular nerves may be ablated by other techniques, including procedures that apply thermal, ultrasonic, laser, microwave, and/or other related energy sources to the vessel wall.

It may be beneficial to provide apparatuses and methods including, but not limited to, renal nerve modulation systems as well as methods of use and manufacture thereof, that increase and/or otherwise enhance the efficacy of the electrical energy delivered within an intended treatment zone of a patient's body.

SUMMARY

The present disclosure is directed to an intravascular nerve modulation system for performing nerve ablation.

Accordingly, one illustrative embodiment includes an intravascular nerve modulation system having an outer elongate shaft having a proximal end, a distal end, and a lumen extending therebetween and an inner elongate shaft having a proximal end and a distal end. The system may further include an expandable basket having a proximal end and a distal end. The proximal end of the expandable basket may be affixed adjacent to the distal end of the outer elongate shaft. An electrode assembly may be affixed to an outer surface of the expandable basket and an outer cover may be disposed over the outer surface of the expandable basket and at least a portion of the electrode assembly. In some embodiments, the distal end of the basket may be affixed to or adjacent to the distal end of the inner tubular such that in an expanded configuration, the distal end of the expandable basket and the proximal end of the expandable basket may have a tapered cross-sectional area. In other embodiments, in an expanded configuration the distal end of the expandable basket may have a larger cross-sectional area than the proximal end of the expandable basket.

The above summary of some embodiments is not intended to describe each disclosed embodiment or every implementation of the present disclosure. The Figures, and Detailed Description, which follow, more particularly exemplify these embodiments.

BRIEF DESCRIPTION OF DRAWINGS

The invention may be more completely understood in consideration of the following detailed description of various embodiments in connection with the accompanying drawings, in which.

Figure 1:
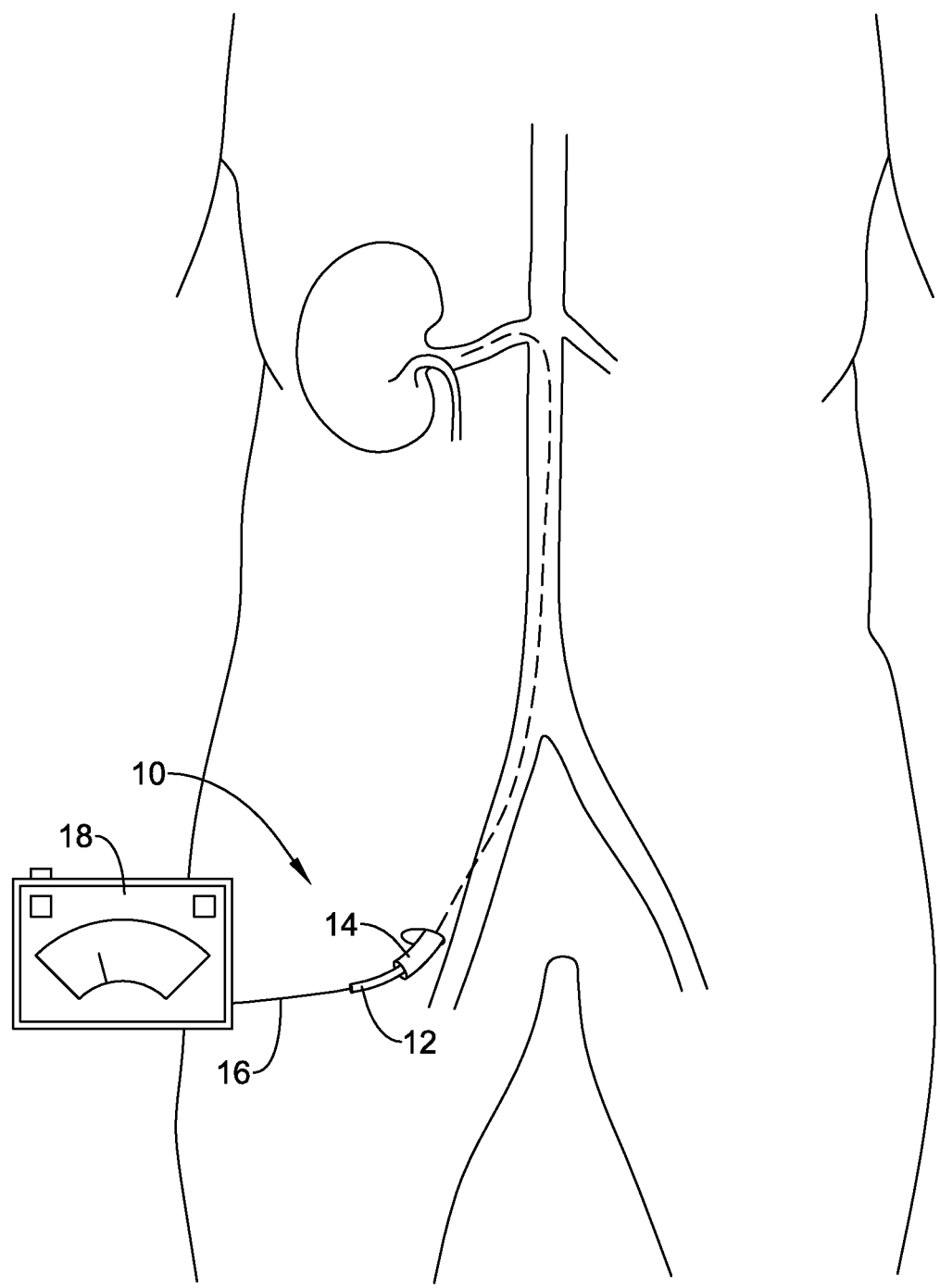
FIG. 1 is a schematic view illustrating a renal nerve modulation system in situ.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, wherein like reference numerals indicate like elements throughout the several views. The drawings, which are not necessarily to scale, are not intended to limit the scope of the claimed invention. The detailed description and drawings illustrate exemplary embodiments of the claimed invention.

All numbers used or otherwise included herein should be considered to be modified by the term "about." The disclosure or recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular indefinite articles "a," "an," and the definite article "the," should be considered to include or otherwise cover both single and plural referents, unless the content clearly dictates otherwise. In other words, these articles are applicable to one or more referents. As used in this specification and the appended claims, the term "or" should be considered to mean "and/or," unless the content clearly dictates otherwise.

References in the specification to "an embodiment," "some embodiments," "other embodiments," etc., indicate that the embodiment described may include a particular feature, structure, or characteristic, but every embodiment may not necessarily include the particular feature, structure, or characteristic. Moreover, such phrases do not necessarily refer to the same embodiment. Further, if a particular feature, structure, or characteristic is described in connection with an embodiment, then it would be within the knowledge of one skilled in the art to affect such feature, structure, or characteristic in connection with other embodiments, whether or not explicitly described, unless clearly stated to the contrary.

Certain treatments require the temporary or permanent interruption or modification of select nerve function. One example treatment is renal nerve ablation, which is sometimes used to treat conditions related to hypertension, congestive heart failure, diabetes, or other conditions impacted by high blood pressure or salt retention. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many of the devices and methods are disclosed herein in the context of renal nerve modulation through a blood vessel wall. However, devices and methods of other embodiments may be used in other contexts, such as applications other than where nerve modulation and/or ablation are desired. It is contemplated that the devices and methods may be used in other treatment locations and/or applications where nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, cardiac ablation, pulmonary vein isolation, tumor ablation, benign prostatic hyperplasia therapy, nerve excitation or blocking or ablation, modulation of muscle activity, hyperthermia or other warming of tissues, etc. The disclosed methods and apparatus can be applied to any relevant medical procedure, involving both human and non-human subjects. The term modulation refers to ablation and other techniques that may alter the function of affected nerves and other tissue. In some embodiments, a single ablation device may be used to sequentially or simultaneously perform multiple ablations, if desired.

FIG. 1 is a schematic view of an illustrative renal nerve modulation system in situ. The renal nerve modulation system 10 may include one or more conductive element(s) 16 for providing power to a renal nerve modulation device. An illustrative renal nerve modulation device may include an intravascular catheter or nerve modulation device 12 optionally disposed within a delivery sheath or guide catheter 14. The delivery sheath 14 may be adapted to slidably contain the intravascular catheter 12 if a radially expanding distal portion (not shown) of the intravascular catheter 12 is in a non-expanded configuration, as will be discussed in more detail below. A distal end of each of the conductive element(s) 16 is attached to one or more electrodes at a location at or near a distal end of the intravascular catheter 12. A proximal end of each of the conductive element(s) 16 may be connected to a power and control unit 18, which supplies electrical energy used to activate the one or more electrodes. The power and control unit 18 is typically located outside of the patient's body. The electrodes are capable of modulating or ablating tissue upon being suitably activated via the control unit 18.

In the following disclosure, the terms electrode and electrodes may be considered to be equivalent to elements capable of ablating adjacent tissue. The disclosure of "adjacent tissue" is intended to cover any tissue located sufficiently proximate the electrode(s) for ablation, and the locations and distances involved are intended to vary depending on application and/or other factors.

The power and control unit 18 may include monitoring elements to monitor parameters, such as power, temperature, voltage, pulse size, impedance and/or shape, and/or other suitable parameters. The power and control unit 18 may also include, or otherwise be used with, sensors mounted along the renal nerve modulation device, as well as suitable controls for performing the desired procedure. In some embodiments, the control unit 18 may control a radio frequency (RF) electrode. The electrode may be configured to operate at a frequency of approximately 460 kHz. However, any desired frequency in the RF range may be used, for example, from 450-500 kHz. In addition, other types of ablation devices may be used as desired including, but not limited to, devices that involve resistance heating, ultrasound, microwave, and laser technologies. The power and control unit 18 may supply different forms of power to these devices.

Figure 2A:
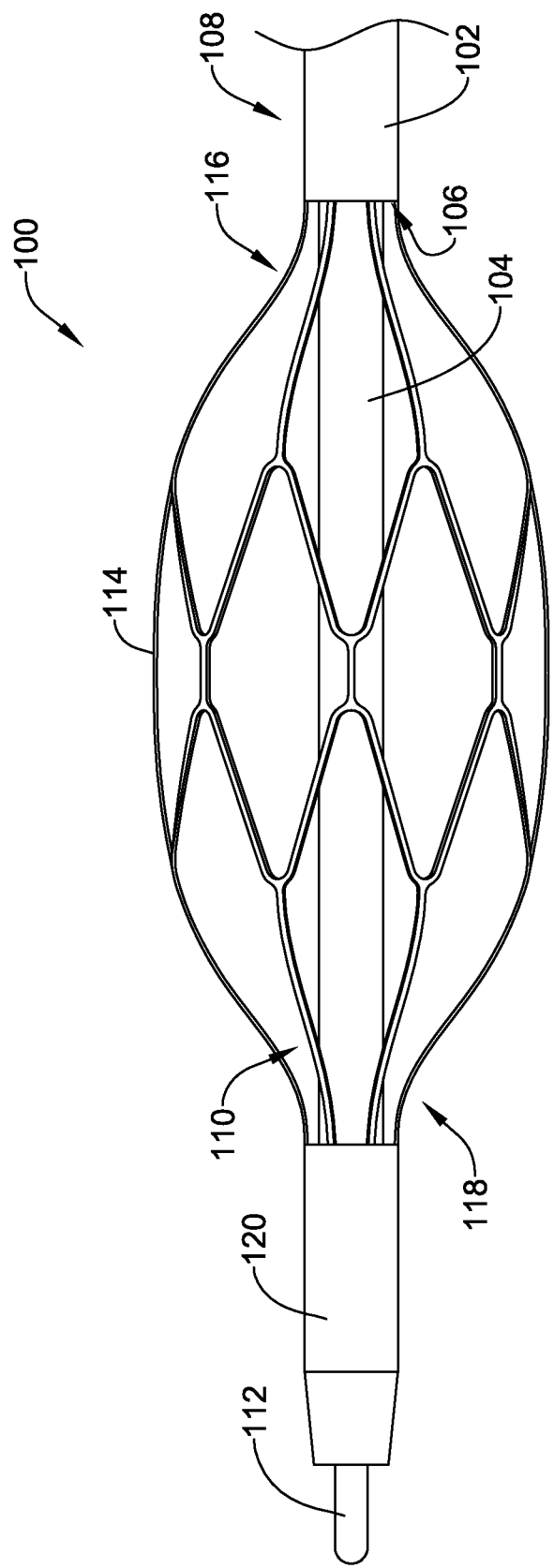
FIGS. 2A-2D illustrate a distal portion of an illustrative renal nerve modulation device.

FIGS. 2A-2D and 3 illustrate a distal portion of an illustrative renal nerve modulation device 100 having a basket structure covered with a coating. Referring first to FIG. 2A, the renal nerve modulation system 100 may include a catheter shaft having an outer elongate shaft 102 and an inner elongate shaft 104. The outer elongate shaft 102 may extend proximally from a distal end region 108 to the proximal end configured to remain outside of a patient's body. The inner elongate shaft 104 may be slidably disposed within a lumen 106 of the outer elongate shaft 102. The inner elongate shaft 104 may extend proximally from a distal end region 110 to a proximal end configured to remain outside of a patient's body. Although not shown, the proximal ends of the inner and/or outer elongate shafts 104, 102 may include a hub attached thereto for connecting other treatment devices or providing a port for facilitating other treatments. It is contemplated that the stiffness of the inner and/or outer elongate shafts 104, 102 may be modified to form a modulation device 100 for use in various vessel diameters and various locations within the vascular tree.

In some instances, the inner and/or outer elongate shafts 104, 102 may have an elongate tubular structure and may include one or more lumens extending therethrough. For instance, in the illustrated embodiment, the outer elongate shaft 102 may include a lumen 106 for slidably receiving the inner tubular shaft 104. The inner tubular shaft 104 may include a lumen (not explicitly shown) having a guidewire wire 112 slidably disposed therein. In some instances, the modulation device 100 may have a fixed wire distal end with no guidewire lumen. These are just examples. In some embodiments, the inner and/or outer elongate shafts 104, 102 may include one or more auxiliary lumens. In some instances, the inner and/or outer elongate shafts 104, 102 may include a separate lumen(s) (not shown) for infusion of fluids, such as saline or dye for visualization or for other purposes such as the introduction of a medical device, and so forth. The fluid may facilitate cooling of the modulation device 100 during the ablation procedure, in addition to the cooling of a body lumen. Further, the lumens may be configured in any way known in the art. For example, the lumen(s) may extend along the entire length of the inner and/or outer elongate shafts 104, 102 such as in an over-the-wire catheter or may extend only along a distal portion of the inner and/or outer elongate shafts 104, 102 such as in a single operator exchange (SOE) catheter. These examples are not intended to be limiting, but rather examples of some possible configurations. While not explicitly shown, the modulation device 100 may further include temperature sensors/wire, an infusion lumen, radiopaque marker bands, fixed guidewire tip, a guidewire lumen, and/or other components to facilitate the use and advancement of the device 100 within the vasculature.

Further, the inner and/or outer elongate shafts 104, 102 may have a relatively long, thin, flexible tubular configuration. In some instances, the inner and/or outer elongate shafts 104, 102 may have a generally circular cross-section, however, other suitable configurations such as, but not limited to, rectangular, oval, irregular, or the like may also be contemplated. In addition, the inner and/or outer elongate shafts 104, 102 may have a cross-sectional configuration adapted to be received in a desired vessel, such as a renal artery. For instance, the inner and/or outer elongate shafts 104, 102 may be sized and configured to accommodate passage through an intravascular path, which leads from a percutaneous access site in, for example, the femoral, brachial, or radial artery, to a targeted treatment site, for example, within a renal artery.

The modulation device 100 may further include an expandable basket 114 having a proximal end 116 and a distal end 118. In the expanded form, the basket 114 may have a tapered proximal end 116 and a tapered distal end 118 and an enlarged central region, although this is not required. In some embodiments, the expandable basket 114 may be laser cut from a generally tubular member to form the desired pattern. While the expandable basket 114 is illustrated as having an open cell, generally stent-like, structure it is contemplated that the basket 114 may be formed to have any of a number of different configurations. For example, in some instances, the basket 114 may be formed from a number of generally longitudinally extending tines or may be formed from one or more filaments that may be woven, braided, knotted, etc. These are just examples. It is contemplated that the use of an expandable basket 114 may eliminate the need for an inflation lumen, thus reducing the overall profile of the modulation system 100.

It is contemplated that the expandable basket 114 can be made from a number of different materials such as, but not limited to, metals, metal alloys, shape memory alloys and/or polymers, as desired, enabling the basket 114 to be expanded into shape when positioned within the body. For example, the expandable basket 114 can be formed from alloys such as, but not limited to, nitinol or Elgiloy®. Depending on the material selected for construction, the basket 114 may be self-expanding or may require an actuation mechanism as will be discussed in more detail below. In some embodiments, fibers may be used to make the expandable basket 114, which may be cored fibers, for example, having an outer shell made of nitinol having a platinum core. It is further contemplated the expandable basket 114 may be formed from polymers including, but not limited to, polyether ether ketone (PEEK), nylon, polyethylene terephthalate (PET), polyimides, polyether block amides, etc.

The proximal end 116 of the basket 114 may be secured to or adjacent to the distal end region 108 of the outer elongate shaft 102. The distal end 118 of the basket 114 may be secured to or adjacent to the distal end region 110 of the inner elongate shaft 104. In some instances, the distal end 118 of the basket 114 may be secured directly to the inner elongate shaft 104. In other instances, the distal end 118 of the basket 114 may be secured to a mounting element 120. The mounting element 120 may be slidably disposed over the inner elongate shaft 104 or may be fixedly secured to the inner elongate shaft 104. As noted above, in some instances, the basket 114 may be self-expanding. It is contemplated that a self-expanding basket 114 may be maintained in a compressed (or collapsed state) when an external force is placed on the basket 114. The basket 114 may then expand when the external force is released. In such an instance, the basket 114 may be formed in the expanded state (as shown in FIG. 2A) and compressed to fit within a delivery sheath. Upon reaching the target location, the delivery sheath can be retracted to deploy the expandable basket 114. It is contemplated that in some instances, the basket may be self-expanding without a capture sheath since the guide sheath could introduce it into the vessel and if the cover material made the basket 114 atraumatic enough so that it could be introduced into the artery while expanded.

In other embodiments, the system 100 may include an actuation mechanism, for example, a pull wire 132 (see FIG. 3), which may be employed to manipulate or actuate the expandable basket 114 between the collapsed and expanded configurations. In an embodiment, the pull wire 132 may be attached to the proximal end 116 or distal end 118 of the basket 114 such that a push-pull actuation of the pull wire 132 may manipulate the expandable basket 114, thus actuating the expandable basket 114 between the collapsed and expanded configurations. In some instances, the pull wire 132 may be pulled proximally to pull the expandable basket 114, moving the expandable basket 114 to the expanded configuration. In addition, the pull wire 132 may be pushed distally to move the expandable basket 114 into the collapsed configuration. Alternatively, the pull wire 132 may be pushed distally, which may allow the expandable basket 114 to move to the expanded state. In such an instance, the pull wire 132 may be pulled proximally, which may allow the expandable basket 114 to move to the collapsed state.

Figure 2B:
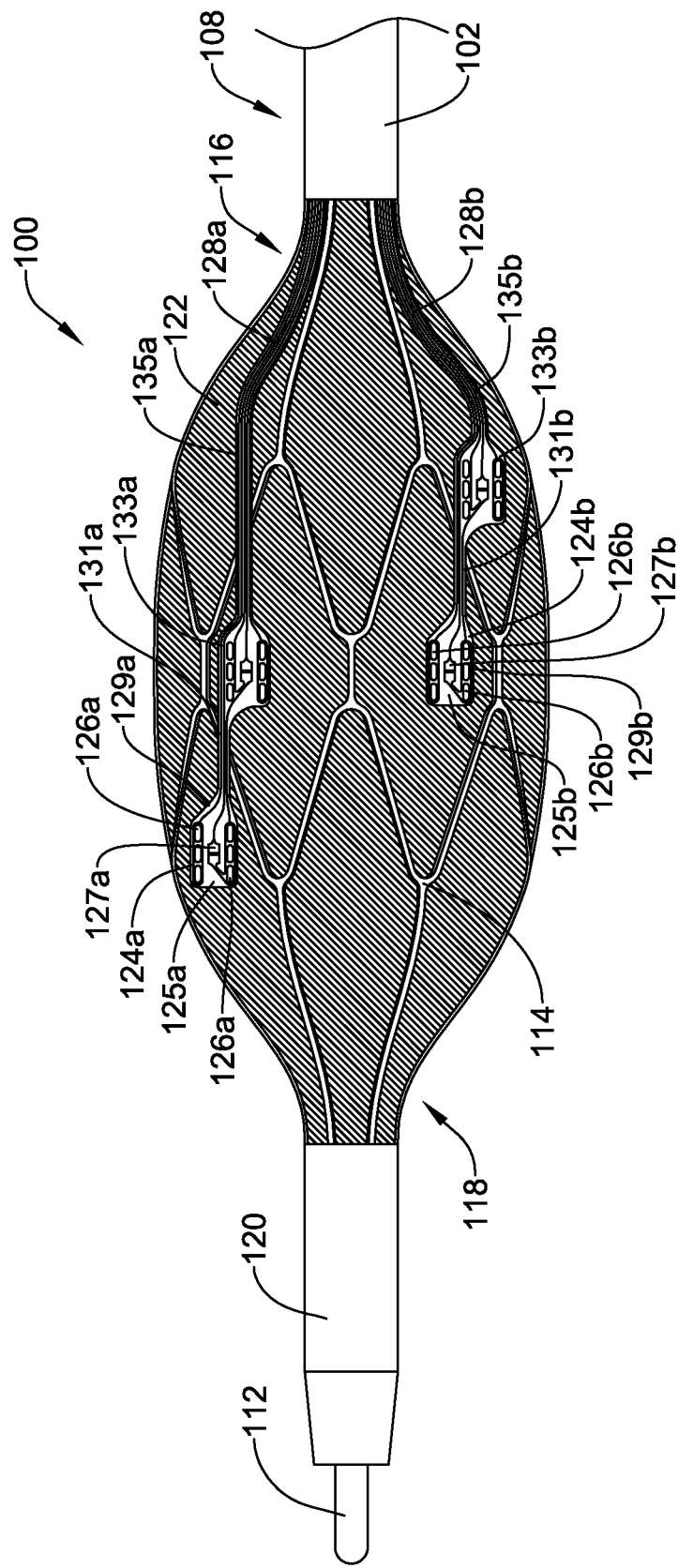

FIG. 2B illustrates the modulation system 100 of FIG. 2A including additional components. The modulation system 100 may further include an inner cover or coating 122 disposed on an inner surface of the expandable basket 114. In some instances, the inner cover 122 may be adhered to the basket 114 using methods commonly known in the art. The inner cover 122 may be made from an elastomeric material, such as, but not limited to: polyurethane, silicone, etc. An elastomeric material may help close the basket 114 to its un-expanded configuration after use. However, in some instances, elastomers such as polyurethane may fail due the heat from ablation. To prevent this, the elastomer could be insulated around the electrodes with a higher temperature material, doped to increase its melt point, (for example, with silica), one may use higher temperature urethanes (for example, aromatics that are dip coated rather than extruded). Alternatively, the cover material could be a less stretchable material, for example, tetrafluoroethylene (Tfe), polyethylene terephthalate (PET), or fabrics (for example, polyester or polymer coated fabrics), which would be less subject to the ablation temperatures. It is contemplated that the inner cover 122 may extend from the proximal end 116 to the distal end 118 of the basket 114. However, this is not required. It is contemplated that the inner cover 122 may extend over any length or partial length of the basket 114 desired, or may not even be present.

The modulation system 100 may further include one or more electrode assemblies 124a, 124b positioned on a surface of the expandable basket 114 and/or inner cover 122 for delivering RF energy to a desired treatment region. In some instances, one or more electrode assemblies 124a, 124b may be positioned on a surface of an outer cover 130

Figure 2C:
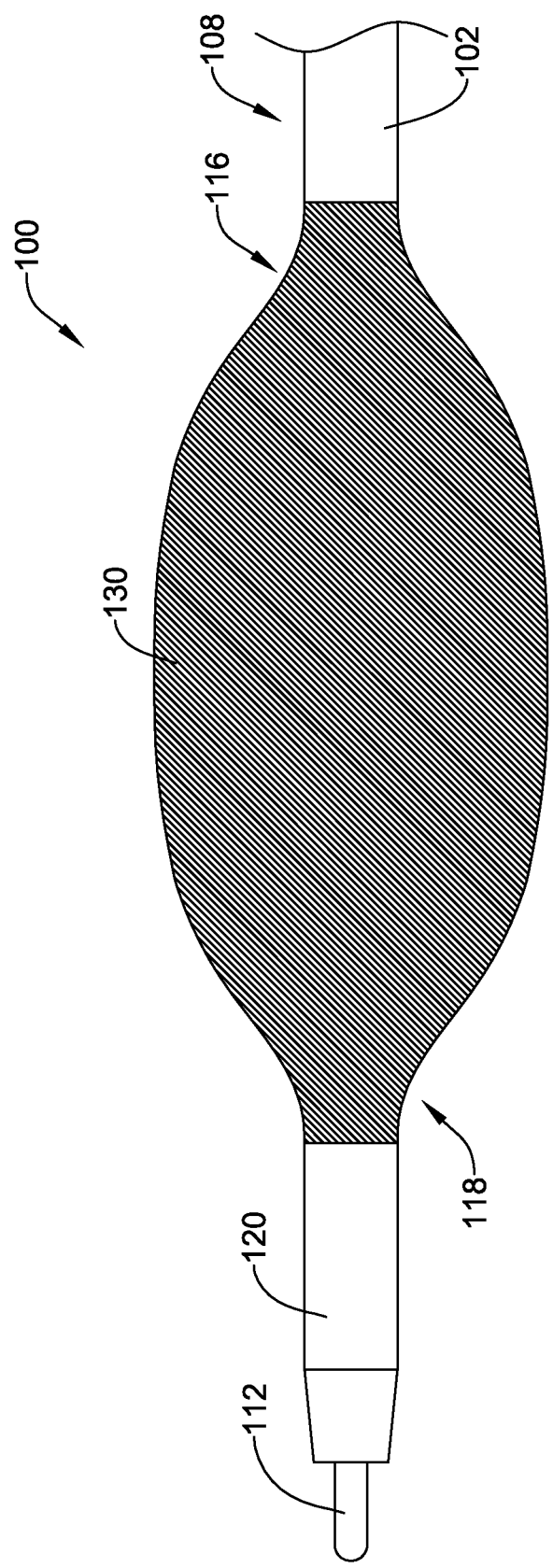

(see FIG. 2C). An exemplary electrode assembly useable with the embodiments disclosed herein is disclosed in U.S. Patent Application Ser. No. 61/856,523 entitled "Spiral Bipolar Electrode Renal Denervation Balloon", the full disclosure of which is incorporated by reference herein. Each electrode assembly 124a, 124b may be constructed as a flexible circuit having a plurality of layers. Such layers may be continuous or non-contiguous, i.e., made up of discrete portions. A base layer 125a, 125b of insulation may provide a foundation for the electrode assemblies 124a, 124b. The base layer 125a, 125b may be constructed from a flexible polymer such as polyimide, although other materials are contemplated. However, the modulation systems disclosed herein are not intended to be limited to the use of only flexible circuits to deliver the treatment energy to the treatment region. It is contemplated that the energy delivery devices may be of any type desired. A conductive layer made up of a plurality of discrete traces may be layered on top of the base layer 125a, 125b. The conductive layer may be, for example, a layer of electrodeposited copper. Other materials are also contemplated. An insulating layer may be discretely or continuously layered on top of the conductive layer, such that the conductive layer may be fluidly sealed between the base layer 125a, 125b and the insulating layer. Like the base layer 125a, 125b, the insulating layer may be constructed from a flexible polymer such as polyimide, although other materials are contemplated. In other embodiments, the insulating layer may be a complete or partial polymer coating, such as PTFE or silicone. Other materials are also contemplated.

The electrode assemblies 124a, 124b may include a distal electrode pad 129a, 129b. In this region, the base layer 125a, 125b may form a rectangular shape. This is not intended to be limiting. Other shapes are contemplated. While not explicitly shown, the electrode assemblies 124a, 124b may include a plurality of openings to provide for added flexibility, and the pads and other portions of the assemblies may include rounded or curved corners, transitions and other portions. In some instances, the openings and rounded/curved features may enhance the assembly's resistance to delamination from its expandable device, as may occur, in some instances, when the expandable device is repeatedly expanded and collapsed (which may also entail deployment from and withdrawal into a protective sheath), such as may be needed when multiple sites are treated during a procedure. It is contemplated that in some embodiments, the base layer 125a, 125b may not be required. For example, the electronic components, electrodes and thermistors, could be mounted on the basket 114 or in the inner cover 122 or outer cover 130 (see FIGS. 2C and 2D) and the conductive traces could be fine wires, or could be traced inside the inner cover 122 or outer cover 130 using for example, Micropen technology.

The distal electrode pad 129a, 129b may include a plurality of discrete traces 128a, 128b layered on top of the base layer 125a, 125b. These traces may include a ground trace, an active electrode trace, and a sensor trace (not explicitly shown) for electrically connecting electrodes, components, and/or a power and control unit. The ground trace may include an elongated electrode support laterally offset from a sensor ground pad. The sensor ground pad may be electrically coupled to the elongated support of the ground trace and may be centrally located on the distal electrode pad. A bridge may connect a distal most portion of the sensor ground pad to a distal portion of the elongated electrode support of the ground trace. The bridge may taper down in width as it travels to the sensor ground pad. In some embodiments, the bridge may have a relatively uniform and thin width to enable a desired amount of flexibility. The elongated electrode support may taper down in width at its proximal end; however, this is not required. In some embodiments, the elongated electrode support may abruptly transition to a much thinner trace at its proximal portion, to enable a desired amount of flexibility. The shape and position of the traces may also be optimized to provide dimensional stability to the electrode assembly 124a, 124b as a whole, so as to prevent distortion during deployment and use. The ground trace and active electrode trace may share a similar construction. The active electrode trace may also include an elongated electrode support.

The ground electrode trace and active electrode trace may include a plurality of electrodes 126a, 126b. Three electrodes 126a, 126b may be provided for each electrode trace, however, more or less may be used. Additionally, each electrode 126a, 126b may have radiused corners to reduce tendency to snag on other devices and/or tissue. Although the above description of the electrodes 126a, 126b and the traces associated with them has been described in the context of a bi-polar electrode assembly, those of skill in the art will recognize that the same electrode assembly may function in a monopolar mode as well. For instance, as one non-limiting example, the electrodes associated with active electrode traces may be used as monopolar electrodes, with ground trace disconnected during energization of those electrodes.

In some embodiments, the electrodes 126a, 126b may be gold pads approximately 0.038 mm thick from the conductive layer and that may protrude about 0.025 mm above the insulating layer 125a, 125b. Without limiting the use of other such suitable materials, gold may be a good electrode material because it is very biocompatible, radiopaque, and electrically and thermally conductive. In other embodiments, the electrode thickness of the conductive layer may range from about 0.030 mm to about 0.051 mm. At such thicknesses, relative stiffness of the electrodes 126a, 126b, as compared to, for example, the copper conductive layer, may be high. Because of this, using a plurality of electrodes, as opposed to a single electrode, may increase flexibility. In other embodiments, the electrodes may be as small as about 0.5 mm by about 0.2 mm or as large as about 2.2 mm by about 0.6 mm for electrode 126a, 126b.

The sensor trace may be centrally located on the distal electrode pad 129a, 129b and may include a sensor power pad facing the sensor ground pad. These pads may connect to power and ground poles of a temperature sensor 127a, 127b, such as a thermocouple (for example, Type T configuration: Copper/Constantan) or thermistor. The temperature sensor 127a, 127b may be proximately connected to the sensor power pad and may be distally connected to the sensor ground pad. To help reduce overall thickness, the temperature sensor 127a, 127b may be positioned within an opening within the base layer 125a, 125b.

From the distal electrode pad 129a, 129b, the combined base layer 125a, 125b, conductive layer, and insulating layer may reduce in lateral width to an intermediate tail 131a, 131b. Here, the conductive layer may be formed to include an intermediate ground line, intermediate active electrode line, and intermediate sensor line, which may be respectively coextensive traces of the ground trace, active electrode trace, and sensor trace of the distal electrode pad 129a, 129b.

From the intermediate tail 131a, 131b, the combined base layer 125a, 125b, conductive layer 204, and insulating layer 206 may increase in lateral width to form a proximal electrode pad 133*a*, 133*b*. The proximal electrode pad 133*a*, 133*b* may be constructed similarly to the distal electrode pad 129*a*, 129*b*, with the electrode geometry and temperature sensor arrangement being essentially identical, although various differences may be present. However, as shown, the proximal electrode pad 133*a*, 133*b* may be laterally offset from the distal electrode pad 129*a*, 129*b* with respect to a central axis extending along the intermediate ground line. The intermediate active electrode line and intermediate sensor line may be laterally coextensive with the proximal electrode pad 133*a*, 133*b* on parallel respective axes with respect to the central axis.

From the proximal electrode pad 133*a*, 133*b*, the combined base layer 125*a*, 125*b*, conductive layer, and insulating layer may reduce in lateral width to form a proximal tail 135*a*, 135*b*. The proximal tail 135*a*, 135*b* may include a proximal ground line, proximal active electrode line, and proximal sensor line, as well the intermediate active electrode line and intermediate sensor line. The proximal tail 135*a*, 135*b* may include connectors (not shown) to enable coupling to one or more sub-wiring harnesses and/or connectors and ultimately to a power and control unit. Each of these lines may be extended along parallel respective axes with respect to the central axis.

As shown, the electrode assembly 124*a*, 124*b* may have an asymmetric arrangement of the distal electrode pad 129*a*, 129*b* and proximal electrode pad 133*a*, 133*b*, about a central axis. Further, the ground electrodes of both electrode pads may be substantially aligned along the central axis, along with the intermediate and proximal ground lines. It has been found that this arrangement may present certain advantages. For example, by essentially sharing the same ground trace, the width of the proximal tail may be only about one and a half times that of the intermediate tail 131*a*, 131*b*, rather than being approximately twice as wide if each electrode pad had independent ground lines. Thus, the proximal tail 135*a*, 135*b* may be narrower than two of the intermediate tails 131*a*, 131*b*.

Further, arranging the electrode pads to share a ground trace may allow control of which electrodes will interact with each other. The various electrode pads may be fired and controlled using solid state relays and multiplexing with a firing time ranging from about 100 microseconds to about 200 milliseconds or about 10 milliseconds to about 50 milliseconds. For practical purposes, the electrode pads may appear to be simultaneously firing yet stray current between adjacent electrode pads of different electrode assemblies 124*a*, 124*b* may be prevented by rapid firing of electrodes in micro bursts. This may be performed such that adjacent electrode pads of different electrode pad assemblies 124*a*, 124*b* are fired out of phase with one another. Thus, the electrode pad arrangement of the electrode assembly may allow for short treatment times—about 10 minutes or less of total electrode firing time, with some approximate treatment times being as short as about 10 seconds, with an exemplary embodiment being about 30 seconds. Some benefits of short treatment times may include minimization of post-operative pain caused when nerve tissue is subject to energy treatment, shortened vessel occlusion times, reduced occlusion side effects, and quick cooling of collateral tissues by blood perfusion due to relatively minor heat input to luminal tissue.

Figure 4:
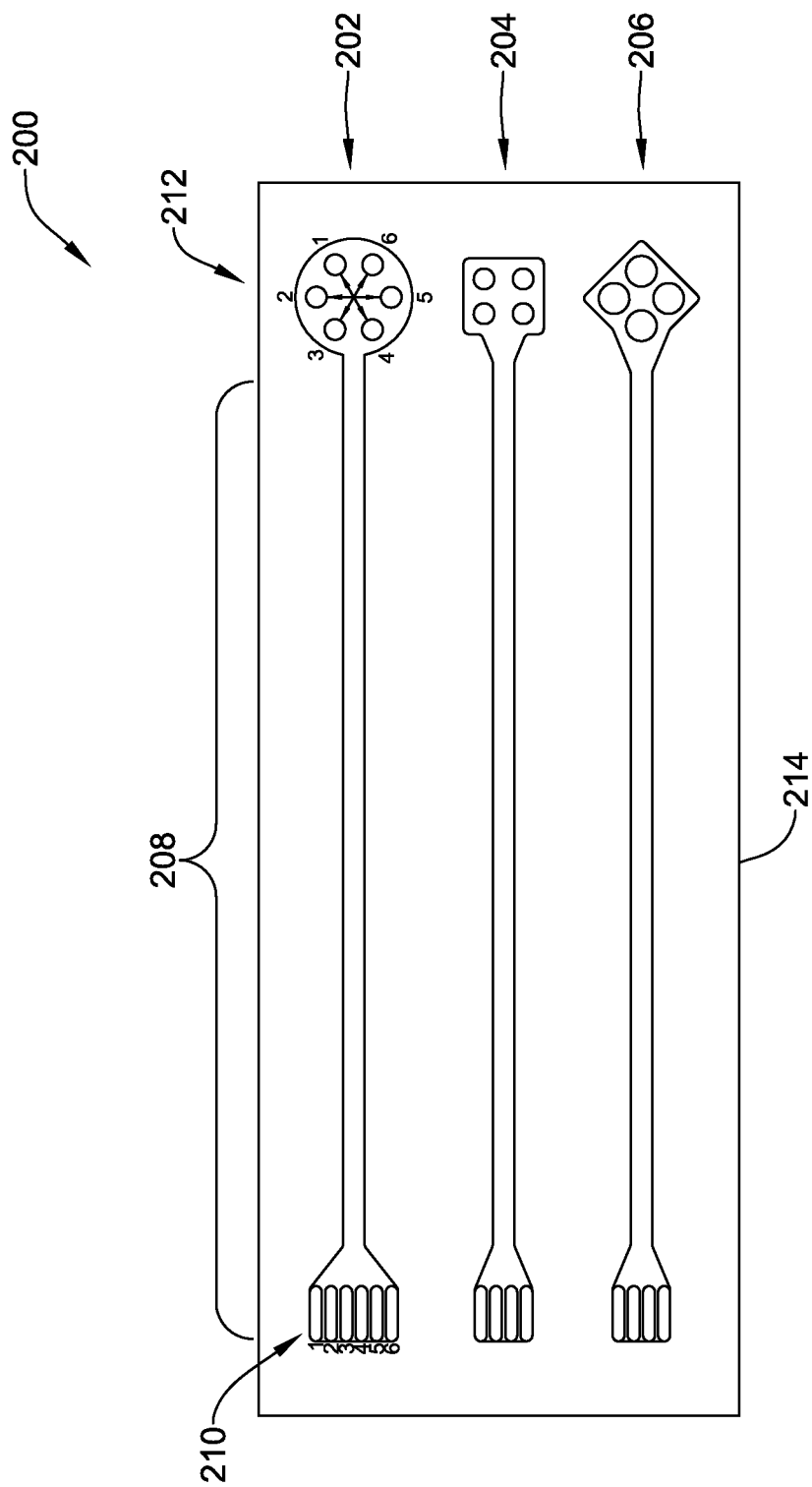
FIG. 4 illustrates some illustrative electrode assemblies.

Referring now to FIG. 4, an illustrative flex circuit panel 200 having flexible circuits 202, 204, and 206 is shown. Each of the flex circuits 202, 204, 206 may include electrically conductive leads 208 that extend between proximal electrical contacts 210 and distal electrodes 212. Leads 208 may be supported by a flexible polymer substrate 214. However, this is not required. It is contemplated that the leads 208, proximal electrical contacts 210, and/or distal electrodes 212 may be mounted directly to any of the expandable baskets or frameworks described herein or to any of the covers or coatings described herein. In some instances, the substrate 214 may be cut around and/or between the electrical components of the circuit to mount the circuits 202, 204, 206 to the desired structure. The electrodes 212 may be positioned adjacent the distal end of a modulation system while the leads 208 may extend proximally along the device such that proximal electrical contact 210 may be electrical coupled to a power and control unit, such as power and control unit 18 shown in FIG. 1. One or more flex circuits 202, 204, and 206 may be mounted to the modulation device. It is contemplated that there may be any number of flex circuits desired based on the desired treatment region and the size of the device. In some instances the electrodes 212 of each flex circuit 202, 204, 206 may optionally provide a grouping or sub-array of electrodes for treating an associated portion or region of a target tissue. Alternative sub-arrays may be provided among electrodes of different flex circuits, may be defined by programmable logic of the processor, and/or may comprise any of a wide variety of alternative electrode circuit structures, with the sub-arrays often being employed for multiplexing or treating the region of target tissue with a plurality of differing electrical energy paths through the tissue.

Still referring to FIG. 4, multiplexing between selected electrodes of an array or sub-array can be effected by selectively energizing electrode pairs, with the target tissue region for the sub-array being disposed between the electrodes of the pairs so that the energy passes therethrough. For example, a pair of electrodes selected from electrodes 1, 2, 3, 4, 5, and 6 of flex circuit 202 (with the selected electrodes optionally being positioned opposite each other) may be energized and then turned off, with another pair then being energized, and so forth. The firing order might be 1 and 4, then 2 and 5, then 3 and 6. Bipolar potentials between the electrodes of the pair can induce current paths in the same general tissue region, with the power dissipated into the tissue optionally remaining substantially constant. This provides a duty cycle of about Vi with respect to heat and/or losses at each electrode surface. The four electrode configurations of flex circuits 204 and 206 could be used in a similar manner with a 50% duty cycle. Monopolar energy might also be applied using a larger ground pad on the skin of the patient or the like, with the duty cycle optionally being cut in half relative to bipolar energy.

Referring again to FIG. 2B, it is contemplated that the modulation system 100 may include any number of electrode assemblies 124*a*, 124*b* desired based on the size of the modulation device 100 and/or the desired treatment region. For example, the modulation system may include one, two, three, four, five, or more electrode assemblies. It is further contemplated that the electrode assemblies 124*a*, 124*b* may be staggered about the circumference and/or length of the expandable basket 114 such that a maximum number of electrode assemblies 124*a*, 124*b* can be positioned on the modulation device.

FIG. 2C illustrates the modulation system 100 of FIG. 2B including additional components. The modulation system 100 may further include an outer cover or coating 130 disposed on an outer surface of the expandable basket 114 and over the inner cover 122 when so present. The outer cover 130 may be made from an elastomeric material, such as, but not limited to: polyurethane, silicone, etc. An elastomeric material may help close the basket 114 to its un-expanded configuration after use. However, in some instances, elastomers such as polyurethane may fail due the heat from ablation. To prevent this, the elastomer could be insulated around the electrodes with a higher temperature material, doped to increase its melt point, (for example, silica), or it may be fine using higher temperature urethanes (for example, aromatics that are dip coated rather than extruded). Alternatively, the cover material could be a less stretchable material, for example, tetrafluoroethylene (Tfe), polyethylene terephthalate (PET), or fabrics (for example, polyester or polymer coated fabrics), which would be less subject to the ablation temperatures. It is contemplated that the outer cover 130 may extend from the proximal end 116 to the distal end 118 of the basket 114. However, this is not required. It is contemplated that the outer cover 130 may extend over any length or partial length of the basket 114 desired, or may not even be present. The inner and outer covers 122, 130 may be formed of the same material or may be formed from different materials, as desired. In some embodiments, one or both of the inner and/or outer covers 122, 130 may be omitted.

In some instances, the outer cover 130 may be adhered to the inner cover 122 and/or basket 114 using methods commonly known in the art. Together, the inner and outer covers 122, 130 may encase all or part of the electrode assemblies 124a, 124b and the associated electronics. It is contemplated that the inner and outer covers 122, 130 may fix the electrode assemblies 124a, 124b more securely to the expandable basket 114 relative to securing flex circuits to a traditional inflatable balloon as the inner and outer covers 122, 130 sandwich the electrode assemblies 124a, 124b and may be more amenable to covalent adhesive bonding. It is contemplated that affixing the electrode assemblies 124a, 124b between at least the basket 114 and the outer cover 130 may improve electrode fixation to system since such an arrangement may eliminate or reduce electrode catch points is not dependent on adhesive to fix the electrode assemblies 124a, 124b to the modulation system. This may improve the safety of system 100.

Figure 2D:
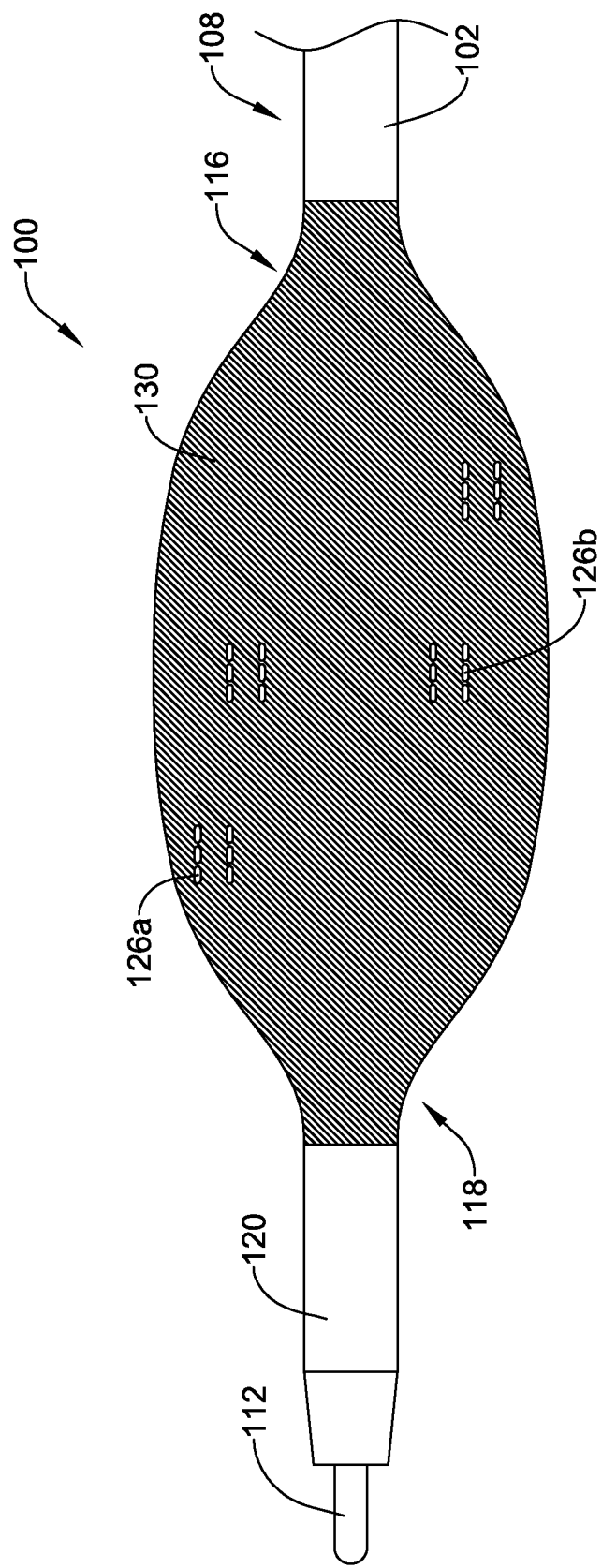

When the outer cover 130 is disposed over the electrodes 126a, 126b, the electrodes may be in insulated contact with the desired treatment region. In some instances, the outer cover 130 may not extend over the electrodes 126a, 126b of the electrode assemblies 124a, 124b, as shown in FIG. 2D. For example, the electrodes 126a, 126b may be coated or covered with a masking material prior to application of the outer cover 130. Once the outer cover 130 has been formed, the masking material may be removed to expose the electrodes 130. In some instances, the outer cover 130 may be disposed over the electrodes 130 and subsequently removed, such as, but not limited to laser ablation. This may allow for the electrodes 326 to directly contact the vessel wall. It is further contemplated that the outer cover 130 may be removed from the electrodes 126 and the electrodes 126 independently (for example using parylene) for insulated contact with the desired treatment region.

In some embodiments, the inner and/or outer covers 122, 130 may include a plurality of holes or apertures (not explicitly shown) at the proximal and distal ends 116, 118 of the basket 114 to allow blood perfusion downstream of the system 100 while the basket 114 is expanded. This may also be preferred with insulated contact ablation to allow blood cooling of the intimal surface of the artery for the purpose of sparing the inside surface of the artery from ablation effects.

Figure 3:
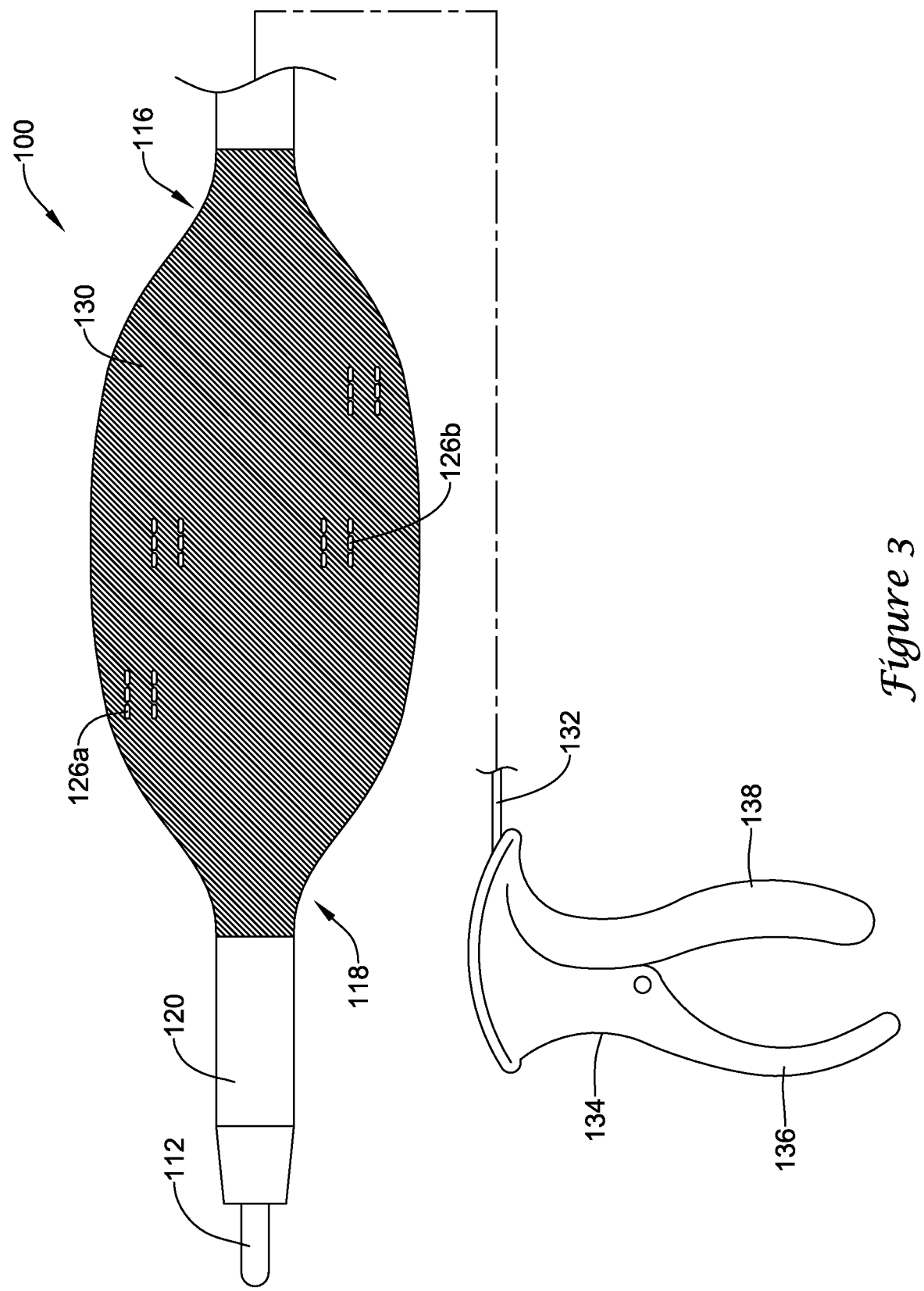
FIG. 3 illustrates the illustrative renal nerve modulation device of FIGS. 2A-2D including an actuation mechanism.

FIG. 3 illustrates the modulation system of FIGS. 2A-2D including an illustrative actuation mechanism 134 for actuating the basket 114 between a collapsed and an expanded position. The actuation mechanism 134 may include a handle or gripping portion 136 and a trigger portion 138. The trigger portion 138 may be affixed to a proximal end of the pull wire 132. As discussed above, a distal end of the pull wire 132 may be attached to or adjacent to the proximal end 116 or the distal end 118 of the basket. The actuation mechanism 134 may be configured such that actuation of the trigger portion 138 results in proximal and/or distal actuation of the pull wire 132 and subsequent expansion or contraction of the basket 114. While the actuation mechanism 134 is illustrated as including a handle 136 and trigger mechanism 138, it is contemplated that the pull wire 132 can be actuated in any manner desired, such as, but not limited to sliding mechanisms, buttons, etc.

The modulation system 100 may be advanced through the vasculature in any manner known in the art. For example, system 100 may include a guidewire lumen to allow the system 100 to be advanced over a previously located guidewire. In some embodiments, the modulation system 100 may be advanced, or partially advanced, within a guide sheath such as the sheath 14 shown in FIG. 1. Once the electrode assemblies 124a, 124b of the modulation system 100 have been placed adjacent to the desired treatment area, the expandable basket 114 may be expanded to bring the electrodes 126a, 126b into contact with the vessel wall.

It is contemplated that expansion of the basket 114 may be controlled such that consistent electrode contact with arterial wall may be accomplished. In some instances, the expanded diameter and/or cross-section of the basket 114 may be adjusted based on the size and/or shape of the vessel. For example, a physician may be able to partially expand the basket 114 in smaller vessels and fully expand the basket 114 in larger vessels. This may allow for fewer catheter sizes to be needed to treat the range of artery diameters (or cross-sectional areas) across patients and may allow for only one catheter to be needed in the approximately 25% of patients where left and right renal artery diameters vary by more than 1 millimeter (mm) since the basket 114 can be expanded to varying diameters. It is further contemplated that the expandable basket may reduce trauma to the arterial wall since the basket 114 would provide less apposition force while providing more complete apposition.

In some embodiments, the basket 114 may be designed to allow the electrode assemblies 124a, 124b to move to move radially independently of each other, allowing for better electrode 126a, 126b apposition as the vessel diameter changes along the length of the vessel. For example, the distal end 118 of the basket 114 could expand to a different cross-section than the proximal end 116 of the basket 114. In this instance, the basket 114 may expand to different degrees to generally conform to a vessel having a varying diameter along the length thereof. In some embodiments, the distal end 118 of the basket 114 may have a smaller or larger cross-section than the proximal end 116 of the basket 114. This may allow the modulation system 100 to be used in non-circumferential vessels as well as tapered vessels while still providing good electrode 126a, 126b contact.

While not explicitly shown, the electrode assemblies 124a, 124b may be connected to a single control unit or to separate control units (such as control unit 18 in FIG. 1) by electrical conductors 128a, 128b. Once the modulation system 100 has been advanced to the treatment region, energy may be supplied to the electrode assemblies 124a, 124b. The amount of energy delivered to the electrode assemblies 124a, 124b may be determined by the desired treatment as well as the feedback provided by other components of the system 100, such as, but not limited to, temperature sensors 127a, 127b.

Once a particular location has been ablated, it may be desirable to perform further ablation procedures at different longitudinal locations. Once the modulation system 100 has been longitudinally repositioned, energy may once again be delivered to the electrode assemblies 124a, 124b. If necessary, the modulation system may be rotated to perform ablation around the circumference of the vessel at each longitudinal location. This process may be repeated at any number of longitudinal locations desired.

When the modulation procedure has been completed, the basket 114 may be collapsed for withdrawal from the body. It is contemplated that basket 114 and electrode assemblies 124a, 124b may collapse in such a manner that "winging" may not occur. This may reduce the force required to withdraw the system 100. It is further contemplated that encasing all or part of the electrode assemblies 124a, 124b and the associated electronics may also reduce potential "catch" points on the modulation system 100 which may also reduce the force required to withdraw the system 100.

Figure 5:
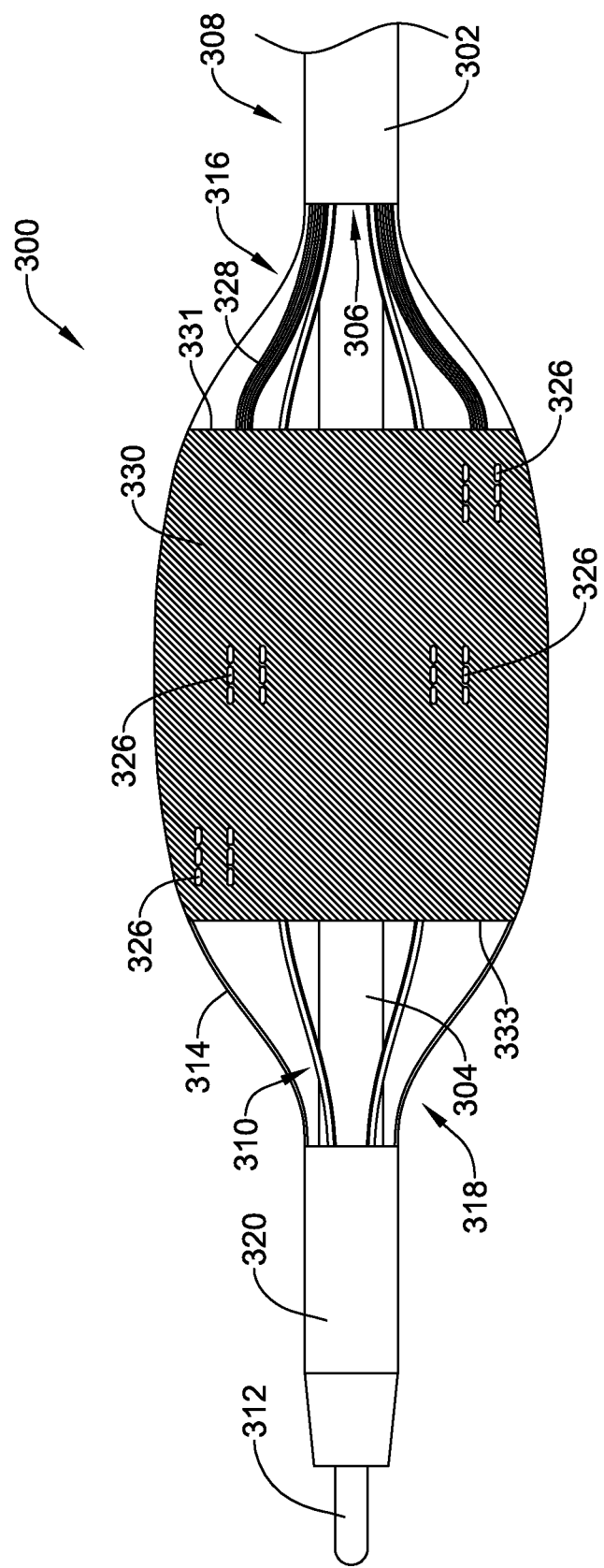
FIG. 5 illustrates a distal portion of another illustrative renal nerve modulation device.

FIG. 5 illustrates a distal portion of another illustrative renal nerve modulation device 300 having a basket structure covered with a coating. The renal nerve modulation system 300 may include an outer elongate shaft 302 having a proximal end and a distal end region 308. The outer elongate shaft 302 may extend proximally from the distal end region 308 to the proximal end configured to remain outside of a patient's body. The modulation device 300 may further include an inner elongate shaft 304 slidably disposed within a lumen 306 of the outer elongate shaft 302. The inner elongate shaft 304 may extend proximally from a distal end region 310 to a proximal end configured to remain outside of a patient's body. The inner tubular shaft 304 may include a lumen (not explicitly shown) having a guidewire wire 312 slidably disposed therein. In some instances, the modulation device 300 may have a fixed wire distal end with no guidewire lumen. Although not shown, the proximal ends of the inner and/or outer elongate shafts 304, 302 may include a hub attached thereto for connecting other treatment devices or providing a port for facilitating other treatments. It is contemplated that the stiffness of the inner and/or outer elongate shafts 304, 302 may be modified to form a modulation device 300 for use in various vessel diameters and various locations within the vascular tree. The inner and/or outer elongate shafts 304, 302 may be similar in form and function to the inner and/or outer elongate shafts 104, 102 described above.

The modulation device 300 may further include an expandable basket 314 having a proximal end 316 and a distal end 318. In some embodiments, the expandable basket 314 may be laser cut from a generally tubular member to form a desired pattern. While not explicitly shown, the expandable basket may have an open cell, generally stent-like, structure. In other instances, it is contemplated that the basket 314 may be formed to have any of a number of different configurations. For example, in some instances, the basket 314 may be formed from a number of generally longitudinally extending tines or may be formed from one or more filaments that may be woven, braided, knotted, etc. These are just examples. Basket 314 may be similar in form and function to basket 114 described above. Depending on the material selected for construction, the basket 314 may be self-expanding or may require an actuation mechanism such as actuation mechanism 134 described above.

The proximal end 316 of the basket 314 may be secured to or adjacent to the distal end region 308 of the outer elongate shaft 302. The distal end 318 of the basket 314 may be secured to or adjacent to the distal end region 310 of the inner elongate shaft 304. In some instances, the distal end 318 of the basket 314 may be secured directly to the inner elongate shaft 304. In other instances, the distal end 318 of the basket 314 may be secured to a mounting element 320. The mounting element 320 may be slidably disposed over the inner elongate shaft 304 or may be fixedly secured to the inner elongate shaft 304. As noted above, in some instances, the basket 314 may be self-expanding. It is contemplated that a self-expanding basket 314 may be maintained in a compressed (or collapsed state) when an external force is placed on the basket 314. The basket 314 may then expand when the external force is released. In such an instance, the basket 314 may be formed in the expanded state (as shown in FIG. 5) and compressed to fit within a delivery or capture sheath. Upon reaching the target location, the delivery sheath can be retracted to deploy the expandable basket 314. In some instances, a vascular access catheter can act as the capture sheath.

In other embodiments, the system 300 may include an actuation mechanism, such as actuation mechanism 134 described above, which may be employed to manipulate or actuate the expandable basket 314 between the collapsed and expanded configurations. In an embodiment, the pull wire may be attached to the proximal end 316 or distal end 318 of the basket 314 such that a push-pull actuation of the pull wire may manipulate the expandable basket 314, thus actuating the expandable basket 314 between the collapsed and expanded configurations. In some instances, the pull wire may be pulled proximally to pull the expandable basket 314, moving the expandable basket 314 to the expanded configuration. In addition, the pull wire may be pushed distally to move the expandable basket 314 into the collapsed configuration. Alternatively, the pull wire may be pushed distally, which may allow the expandable basket 314 to move to the expanded state. In such an instance, the pull wire may be pulled proximally, which may allow the expandable basket 314 to move to the collapsed state.

The modulation system 300 may further include an inner cover or coating (not explicitly shown) disposed on an inner surface of the expandable basket 314. It is contemplated that the inner cover may extend over any length or partial length of the basket 314 desired, or may not even be present. However, this is not required. It is contemplated that in some instances, the inner cover may extend from the proximal end 316 to the distal end 318 of the basket 314.

The modulation system 300 may further include one or more electrode assemblies (not explicitly shown) positioned on an outer surface of the expandable basket 314 and/or inner cover for delivering RF energy to a desired treatment region. The electrode assemblies may be similar in form and function to electrode assemblies 124a, 124b discussed above. However, the modulation systems disclosed herein are not intended to be limited to the use of only flexible circuits to deliver the treatment energy to the treatment region. It is contemplated that the energy delivery devices may be of any type desired. Electrodes 326 on the electrode assemblies may be connected to one another, other electrical components, and/or a power and control unit through one or more electrical conductors 328. The electrodes 326 may be operated in a bi-polar or monopolar mode as desired.

It is contemplated that the modulation system 300 may include any number of electrode assemblies desired based on the size of the modulation device 300 and/or the desired treatment region. For example, the modulation system may include one, two, three, four, five, or more electrode assemblies. It is further contemplated that the electrode assemblies may be staggered about the circumference and/or length of the expandable basket 314 such that a maximum number of electrode assemblies can be positioned on the modulation device.

The modulation system 300 may further include an outer cover or coating 330 disposed on an outer surface of the expandable basket 314 and over the inner cover (when so present). The outer cover 330 may be similar in form and function to outer cover 130 described above. It is contemplated that the outer cover 330 may have a proximal end 331 and a distal end 333. In some instances, the proximal end 331 of the cover 330 may be positioned distal to the proximal end 316 of the basket 314. It is further contemplated that the distal end 333 of the cover 330 may be positioned proximal to the distal end 318 of the basket 314. This may allow for blood perfusion downstream of the modulation system 300 during treatment. However, it is contemplated that either or both the proximal end 331 or the distal end 333 of the outer cover 330 may extend to the proximal or distal end 316, 318 of the frame 314. It is contemplated that the inner cover may have a similar configuration to the outer cover 330. The inner and outer covers 330 may be formed of the same material or may be formed from different materials, as desired. In some embodiments, one or both of the inner and/or outer covers 330 may be omitted.

In some instances, the outer cover 330 may be adhered to the inner cover and/or basket 314 using methods commonly known in the art. Together, the inner and outer covers 330 may encase all or part of the electrode assemblies and the associated electronics. It is contemplated that the inner and outer covers 330 may fix the electrode assemblies more securely to the expandable basket 314 relative to securing flex circuits to a traditional inflatable balloon as the inner and outer covers 330 sandwich the electrode assemblies and may be more amenable to covalent adhesive bonding. In some instances, the outer cover 330 may not extend over the electrodes 326 of the electrode assemblies. For example, the electrodes 326 may be coated or covered with a masking material prior to application of the outer cover 330. Once the outer cover 330 has been formed, the masking material may be removed to expose the electrodes 330. In some instances, the outer cover 330 may be disposed over the electrodes 330 and subsequently removed, such as, but not limited to laser ablation. This may allow for the electrodes 326 to directly contact the vessel wall. In other instances, the outer cover 330 may remain over the electrodes 326 to allow for insulated wall contact. It is further contemplated that the outer cover 330 may be removed from the electrodes 326 and the electrodes 326 independently coated (for example using parylene) for insulated contact with the desired treatment region.

Figure 6A:
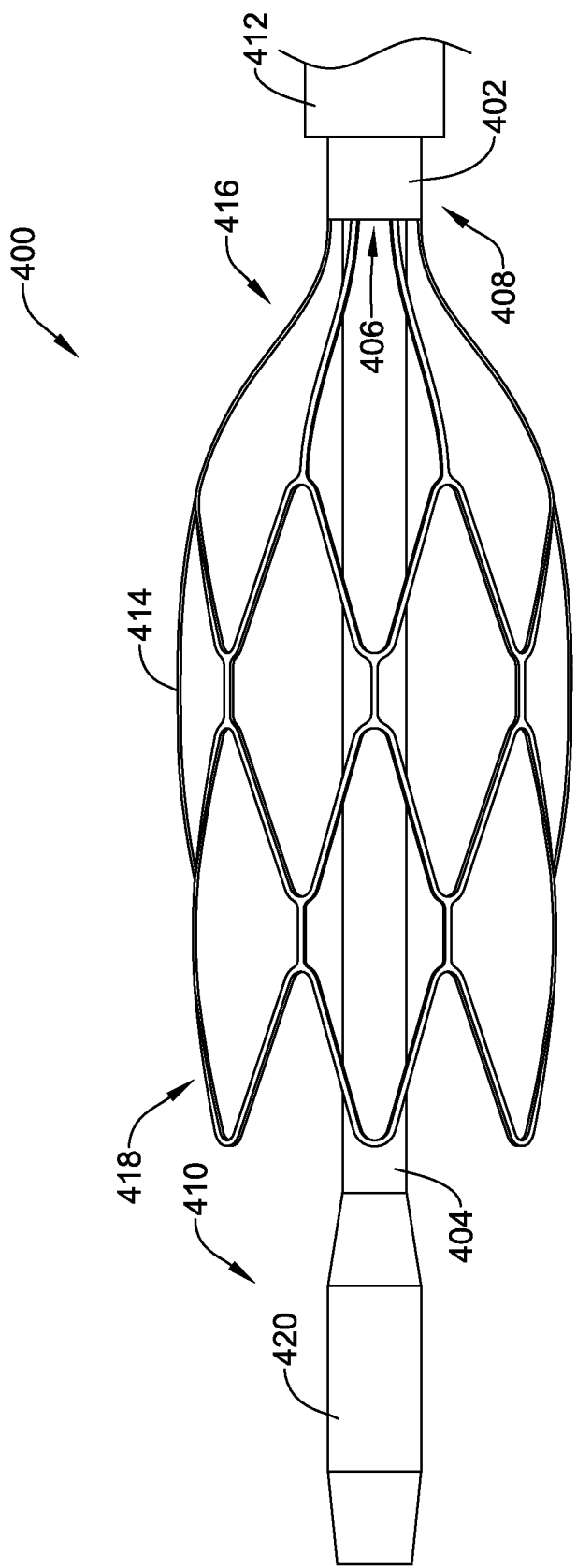
FIGS. 6A-6C illustrate a distal portion of another illustrative renal nerve modulation device.

FIGS. 6A-6C and 7 illustrate a distal portion of an illustrative renal nerve modulation device 400 having a basket structure covered with a coating. Referring first to FIG. 6A, the renal nerve modulation system 400 may include an outer elongate shaft 402 having a proximal end and a distal end region 408. The outer elongate shaft 402 may extend proximally from the distal end region 408 to the proximal end configured to remain outside of a patient's body. The modulation device 400 may further include an inner elongate shaft 404 having an atraumatic tip 420 slidably disposed within a lumen 406 of the outer elongate shaft 402. The inner elongate shaft 404 may extend proximally from a distal end region 410 to a proximal end configured to remain outside of a patient's body. Although not shown, the proximal ends of the inner and/or outer elongate shafts 404, 402 may include a hub attached thereto for connecting other treatment devices or providing a port for facilitating other treatments. It is contemplated that the stiffness of the inner and/or outer elongate shafts 404, 402 may be modified to form a modulation device 400 for use in various vessel diameters and various locations within the vascular tree.

In some instances, the inner and/or outer elongate shafts 404, 402 may have an elongate tubular structure and may include one or more lumens extending therethrough. For instance, in the illustrated embodiment, the outer elongate shaft 402 may include a lumen 406 for slidably receiving the inner tubular shaft 404. The inner tubular shaft 404 may include a lumen (not explicitly shown) for slidably receiving a guidewire wire therein. In some instances, the modulation device 400 may have a fixed wire distal end with no guidewire lumen. These are just examples. In some embodiments, the inner and/or outer elongate shafts 404, 402 may include one or more auxiliary lumens. In some instances, the inner and/or outer elongate shafts 404, 402 may include a separate lumen(s) (not shown) for infusion of fluids or for other purposes such as the introduction of a medical device, and so forth. The fluid may facilitate cooling of the modulation device 400 during the ablation procedure, in addition to the cooling of a body lumen. Further, the lumens may be configured in any way known in the art. For example, the lumen(s) may extend along the entire length of the inner and/or outer elongate shafts 404, 402 such as in an over-the-wire catheter or may extend only along a distal portion of the inner and/or outer elongate shafts 404, 402 such as in a single operator exchange (SOE) catheter. These examples are not intended to be limiting, but rather examples of some possible configurations. While not explicitly shown, the modulation device 400 may further include temperature sensors/wire, an infusion lumen, radiopaque marker bands, fixed guidewire tip, a guidewire lumen, and/or other components to facilitate the use and advancement of the device 400 within the vasculature.

Further, the inner and/or outer elongate shafts 404, 402 may have a relatively long, thin, flexible tubular configuration. In some instances, the inner and/or outer elongate shafts 404, 402 may have a generally circular cross-section, however, other suitable configurations such as, but not limited to, rectangular, oval, irregular, or the like may also be contemplated. In addition, the inner and/or outer elongate shafts 404, 402 may have a cross-sectional configuration adapted to be received in a desired vessel, such as a renal artery. For instance, the inner and/or outer elongate shafts 404, 402 may be sized and configured to accommodate passage through an intravascular path, which leads from a percutaneous access site in, for example, the femoral, brachial, or radial artery, to a targeted treatment site, for example, within a renal artery.

The modulation device 400 may further include an expandable basket 414 having a proximal end 416 and a distal end 418. In some instances, in the expanded state, the proximal end 416 may be tapered while the distal end 418 may have an enlarged cross-sectional area relative to the proximal end 416. In some embodiments, the expandable basket 414 may be laser cut from a generally tubular member to form the desired pattern. While the expandable basket 414 is illustrated as having an open cell, generally stent-like, structure it is contemplated that the basket 414 may be formed to have any of a number of different configurations. For example, in some instances, the basket 414 may be formed from a number of generally longitudinally extending tines or may be formed from one or more filaments that may be woven, braided, knotted, etc. These are just examples.

It is contemplated that the expandable basket 414 can be made from a number of different materials such as, but not limited to, metals, metal alloys, shape memory alloys and/or polymers, as desired, enabling the basket 414 to be expanded into shape when positioned within the body. For example, the expandable basket 414 can be formed from alloys such as, but not limited to, nitinol or Elgiloy®. Depending on the material selected for construction, the basket 414 may be self-expanding or may require an actuation mechanism as will be discussed in more detail below. In some embodiments, fibers may be used to make the expandable basket 414, which may be cored fibers, for example, having an outer shell made of nitinol having a platinum core. It is further contemplated the expandable basket 414 may be formed from polymers including, but not limited to, polyether ether ketone (PEEK), nylon, polyethylene terephthalate (PET), polyimides, polyether block amides, etc.

The proximal end 416 of the basket 414 may be secured to or adjacent to the distal end region 408 of the outer elongate shaft 402. As noted above, in some instances, the basket 414 may be self-expanding. It is contemplated that a self-expanding basket 414 may be maintained in a compressed (or collapsed state) when an external force is placed on the basket 414. The basket 414 may then expand when the external force is released. In such an instance, the basket 414 may be formed in the expanded state (as shown in FIG. 2A) and compressed to fit within a delivery sheath 412. Upon reaching the target location, the delivery sheath 412 can be retracted to deploy the expandable basket 414.

In other embodiments, the system 400 may include an actuation mechanism, for example, a pull wire 432 (see FIG. 7), which may be employed to manipulate or actuate the expandable basket 414 between the collapsed and expanded configurations. In an embodiment, the pull wire 432 may be attached to the proximal end 416 of the basket 414 such that a push-pull actuation of the pull wire 432 may manipulate the expandable basket 414, thus actuating the expandable basket 414 between the collapsed and expanded configurations. In some instances, the pull wire 432 may be pulled proximally to pull the expandable basket 414, moving the expandable basket 414 to the expanded configuration. In addition, the pull wire 432 may be pushed distally to move the expandable basket 414 into the collapsed configuration. Alternatively, the pull wire 432 may be pushed distally, which may allow the expandable basket 414 to move to the expanded state. In such an instance, the pull wire 432 may be pulled proximally, which may allow the expandable basket 414 to move to the collapsed state.

Figure 6B:
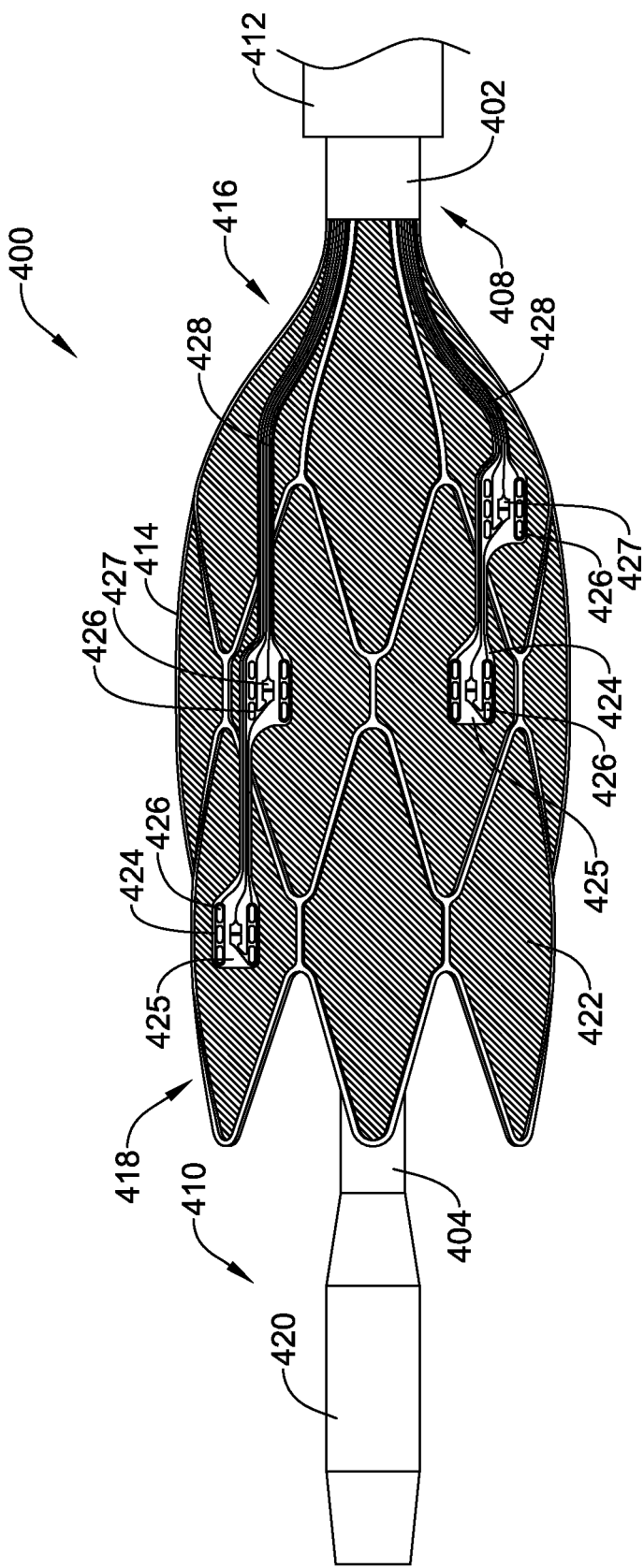

FIG. 6B illustrates the modulation system 400 of FIG. 6A including additional components. The modulation system 400 may further include an inner cover or coating 422 disposed on an inner surface of the expandable basket 414. In some instances, the inner cover 422 may be adhered to the basket 414 using methods commonly known in the art. The inner cover 422 may be made from an elastomeric material, such as, but not limited to: polyurethane, silicone, etc. An elastomeric material may help close the basket 414 to its un-expanded configuration after use. However, in some instances, elastomers such as polyurethane may fail due the heat from ablation. To prevent this, the elastomer could be insulated around the electrodes with a higher temperature material, doped to increase its melt point, (for example, with silica), one may use higher temperature urethanes (for example, aromatics that are dip coated rather than extruded). Alternatively, the cover material could be a less stretchable material, for example, tetrafluoroethylene (Tfe), polyethylene terephthalate (PET), or fabrics (for example, polyester or polymer coated fabrics), which would be less subject to the ablation temperatures. It is contemplated that the inner cover 422 may extend from the proximal end 416 to the distal end 418 of the basket 414. However, this is not required. It is contemplated that the inner cover 422 may extend over any length or partial length of the basket 414 desired, or may not even be present.

The modulation system 400 may further include one or more electrode assemblies 424 positioned on an outer surface of the expandable basket 414 and/or inner cover 422 for delivering RF energy to a desired treatment region. An exemplary electrode assembly useable with the embodiments disclosed herein is disclosed in U.S. Patent Application Ser. No. 61/856,523 entitled "Spiral Bipolar Electrode Renal Denervation Balloon", the full disclosure of which is incorporated by reference herein. The electrodes assemblies 424 may be similar in form and function to electrodes assemblies 124*a*, 124*b* discussed above. Each electrode assembly 424 may be constructed as a flexible circuit having a plurality of layers. A base layer 425 of insulation may provide a foundation for the electrode assemblies 424. The base layer 425 may be constructed from a flexible polymer such as polyimide, although other materials are contemplated. However, the modulation systems disclosed herein are not intended to be limited to the use of only flexible circuits to deliver the treatment energy to the treatment region. It is contemplated that the energy delivery devices may be of any type desired. A conductive layer made up of a plurality of discrete traces may be layered on top of the base layer 425. The electrode assemblies 424 may include a plurality of discrete traces 428 layered on top of the base layer 425. These traces may include a ground trace, an active electrode trace, and a sensor trace (not explicitly shown) for electrically connecting electrodes, components, and/or a power and control unit. The ground electrode trace and active electrode trace may include a plurality of electrodes 426. Three electrodes 426 may be provided for each electrode trace, however, more or less may be used. Additionally, one or more temperature sensors 427 may be provided on each electrode assembly 424.

It is contemplated that the modulation system 400 may include any number of electrode assemblies 424 desired based on the size of the modulation device 400 and/or the desired treatment region. For example, the modulation system may include one, two, three, four, five, or more electrode assemblies. It is further contemplated that the electrode assemblies 424 may be staggered about the circumference and/or length of the expandable basket 414 such that a maximum number of electrode assemblies 424 can be positioned on the modulation device.

Figure 6C:
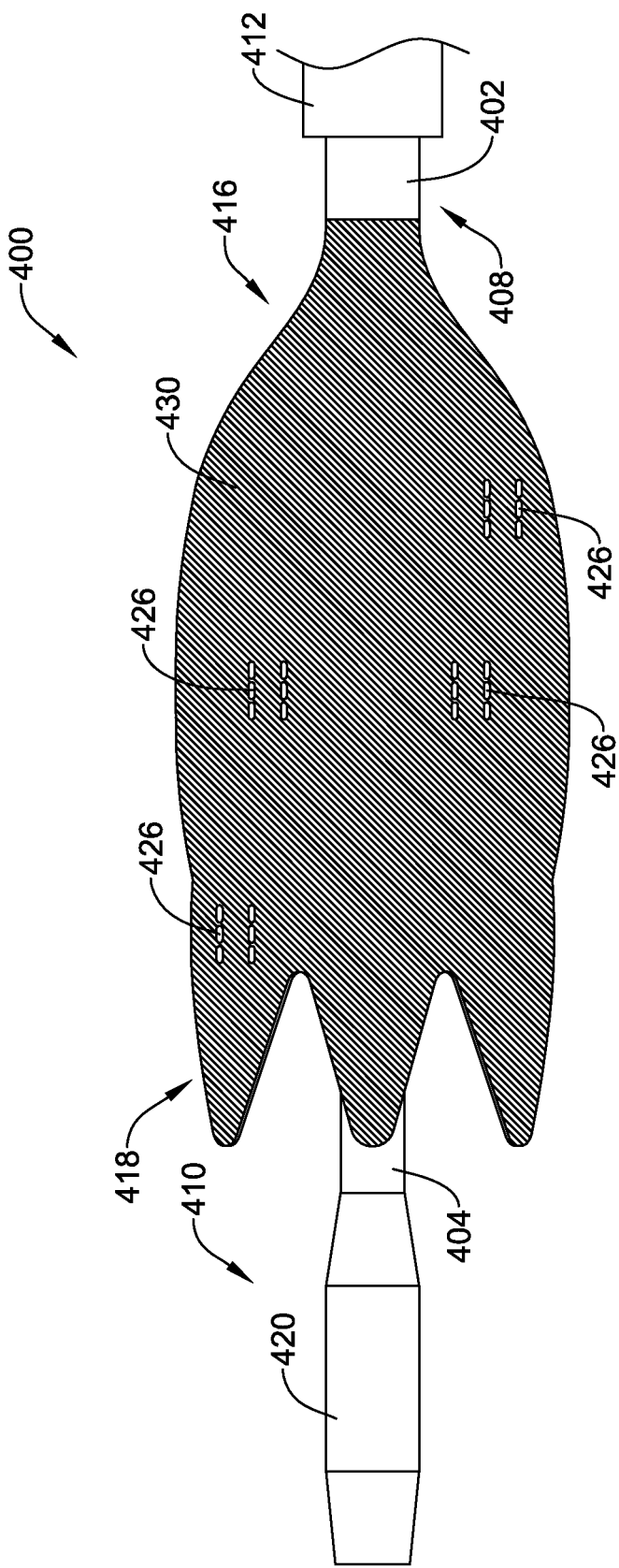

FIG. 6C illustrates the modulation system 400 of FIG. 6B including additional components. The modulation system 400 may further include an outer cover or coating 430 disposed on an outer surface of the expandable basket 414 and over the inner cover 422, when so present. The outer cover 430 may be made from an elastomeric material, such as, but not limited to: polyurethane, silicone, etc. An elastomeric material may help close the basket 414 to its un-expanded configuration after use. However, in some instances, elastomers such as polyurethane may fail due the heat from ablation. To prevent this, the elastomer could be insulated around the electrodes with a higher temperature material, doped to increase its melt point, (for example, silica), or it may be fine using higher temperature urethanes (for example, aromatics that are dip coated rather than extruded). Alternatively, the cover material could be a less stretchable material, for example, tetrafluoroethylene (Tfe), polyethylene terephthalate (PET), or fabrics (for example, polyester or polymer coated fabrics), which would be less subject to the ablation temperatures. It is contemplated that the outer cover 430 may extend from the proximal end 416 to the distal end 418 of the basket 414. However, this is not required. It is contemplated that the outer cover 430 may extend over any length or partial length of the basket 414 desired, or may not even be present. The inner and outer covers 422, 430 may be formed of the same material or may be formed from different materials, as desired. In some embodiments, one or both of the inner and/or outer covers 422, 430 may be omitted.

In some instances, the outer cover 430 may be adhered to the inner cover 422 and/or basket 414 using methods commonly known in the art. Together, the inner and outer covers 422, 430 may encase all or part of the electrode assemblies 424 and the associated electronics. It is contemplated that the inner and outer covers 422, 430 may fix the electrode assemblies 424 more securely to the expandable basket 414 relative to securing flex circuits to a traditional inflatable balloon as the inner and outer covers 422, 430 sandwich the electrode assemblies 424 and may be more amenable to covalent adhesive bonding.

In some instances, the outer cover 430 may not extend over the electrodes 426 of the electrode assemblies 42. For example, the electrodes 426 may be coated or covered with a masking material prior to application of the outer cover 430. Once the outer cover 430 has been formed, the masking material may be removed to expose the electrodes 430. In some instances, the outer cover 430 may be disposed over the electrodes 430 and subsequently removed, such as, but not limited to laser ablation. This may allow for the electrodes 426 to directly contact the vessel wall. In other instances, the outer cover 430 may remain over the electrodes 426 to allow for insulated wall contact. It is further contemplated that the outer cover 430 may be removed from the electrodes 426 and the electrodes 426 independently coated (for example using parylene) for insulated contact with the desired treatment region.

Figure 7:
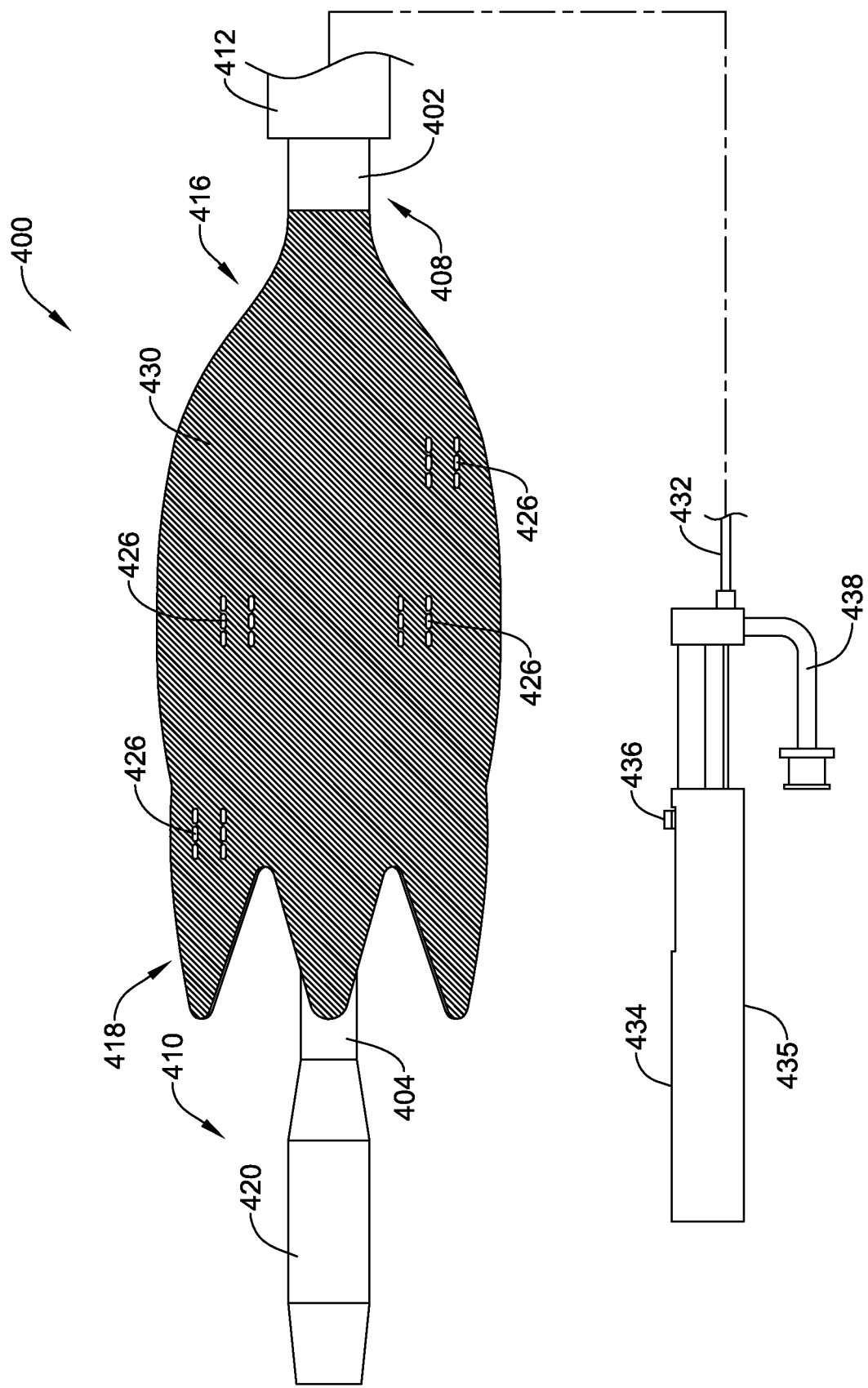
FIG. 7 illustrates the illustrative renal nerve modulation device of FIGS. 6A-6C including an actuation mechanism.

FIG. 7 illustrates the modulation system of FIGS. 6A-6C including an illustrative actuation mechanism 434 for actuating the basket 414 between a collapsed and an expanded position. The actuation mechanism 434 may include a handle or gripping portion 435 and a sliding mechanism 436. The sliding mechanism 436 may be affixed to a proximal end of the pull wire 432. As discussed above, a distal end of the pull wire 432 may be attached to or adjacent to the proximal end 416 of the basket. The actuation mechanism 434 may be configured such that actuation of the sliding mechanism 436 results in proximal and/or distal actuation of the pull wire 432 and subsequent expansion or contraction of the basket 414. While the actuation mechanism 434 is illustrated as including a handle 435 and sliding mechanism 436, it is contemplated that the pull wire 432 can be actuated in any manner desired, such as, but not limited to triggers, buttons, etc. For example, the actuation mechanism 434 may be similar in form and function to actuation mechanism 134 described above.

Figure 8:
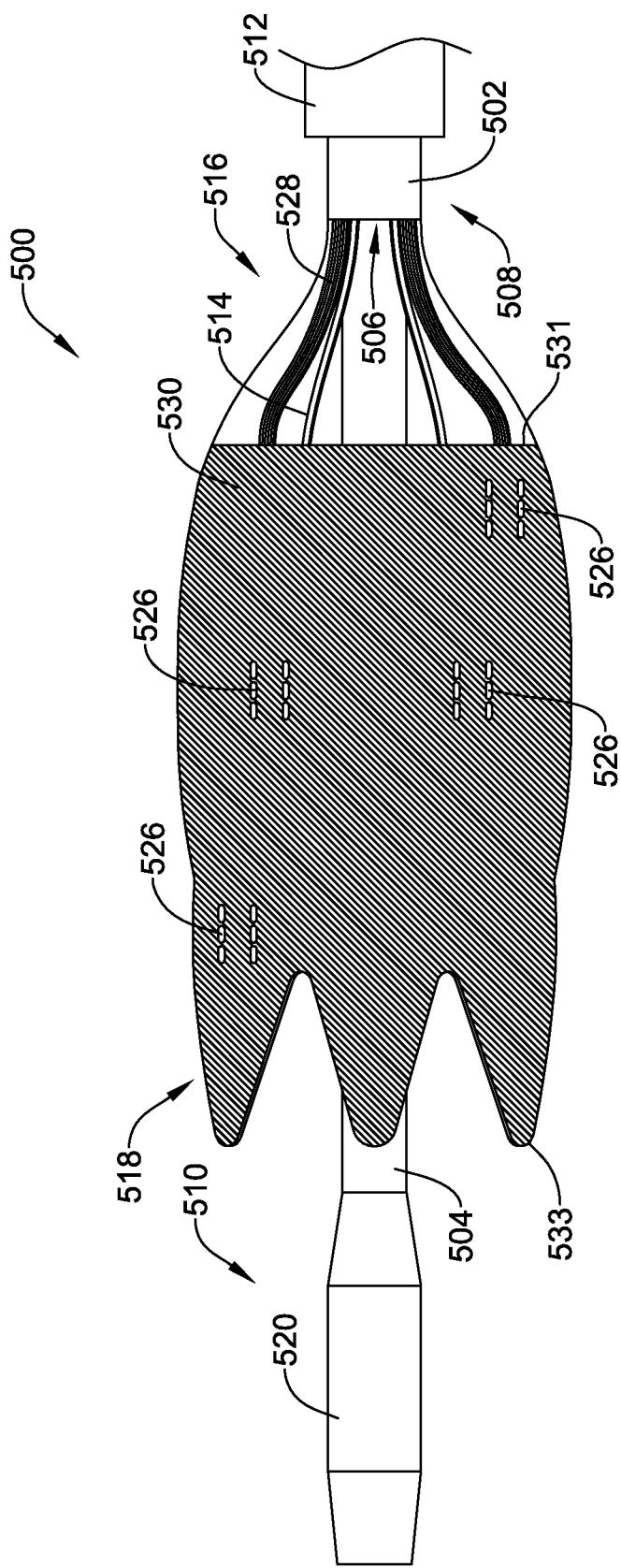
FIG. 8 illustrates a distal portion of another illustrative renal nerve modulation device.

FIG. 8 illustrates a distal portion of another illustrative renal nerve modulation device 500 having a basket structure covered with a coating. The renal nerve modulation system 500 may include an outer elongate shaft 502 having a proximal end and a distal end region 508. The outer elongate shaft 502 may extend proximally from the distal end region 508 to the proximal end configured to remain outside of a patient's body. The modulation device 500 may further include an inner elongate shaft 504 having an atraumatic tip 520 slidably disposed within a lumen 506 of the outer elongate shaft 502. The inner elongate shaft 504 may extend proximally from a distal end region 510 to a proximal end configured to remain outside of a patient's body. The inner tubular shaft 504 may include a lumen (not explicitly shown) for slidably receiving a guidewire wire therein. In some instances, the modulation device 500 may have a fixed wire distal end with no guidewire lumen. Although not shown, the proximal ends of the inner and/or outer elongate shafts 504, 502 may include a hub attached thereto for connecting other treatment devices or providing a port for facilitating other treatments. It is contemplated that the stiffness of the inner and/or outer elongate shafts 504, 502 may be modified to form a modulation device 500 for use in various vessel diameters and various locations within the vascular tree. The inner and/or outer elongate shafts 504, 502 may be similar in form and function to the inner and/or outer elongate shafts 104, 404, 102, 402 described above.

The modulation device 500 may further include an expandable basket 514 having a proximal end 516 and a distal end 518. In some instances, in the expanded state, the proximal end 516 may be tapered while the distal end 518 may have an enlarged cross-sectional area relative to the proximal end 516. In some embodiments, the expandable basket 514 may be laser cut from a generally tubular member to form a desired pattern. While not explicitly shown, the expandable basket may have an open cell, generally stent-like, structure. In other instances, it is contemplated that the basket 514 may be formed to have any of a number of different configurations. For example, in some instances, the basket 514 may be formed from a number of generally longitudinally extending tines or may be formed from one or more filaments that may be woven, braided, knotted, etc. These are just examples. Basket 514 may be similar in form and function to basket 414 described above. Depending on the material selected for construction, the basket 514 may be self-expanding or may require an actuation mechanism such as actuation mechanism 134, 434 described above.

The proximal end 516 of the basket 514 may be secured to or adjacent to the distal end region 508 of the outer elongate shaft 502. As noted above, in some instances, the basket 514 may be self-expanding. It is contemplated that a self-expanding basket 514 may be maintained in a compressed (or collapsed state) when an external force is placed on the basket 514. The basket 514 may then expand when the external force is released. In such an instance, the basket 514 may be formed in the expanded state (as shown in FIG. 8) and compressed to fit within a delivery sheath 512. Upon reaching the target location, the delivery sheath 512 can be retracted to deploy the expandable basket 514.

In other embodiments, the system 500 may include an actuation mechanism, such as actuation mechanism 134, 434 described above, which may be employed to manipulate or actuate the expandable basket 514 between the collapsed and expanded configurations. In an embodiment, a pull wire may be attached to the proximal end 516 of the basket 514 such that a push-pull actuation of the pull wire may manipulate the expandable basket 514, thus actuating the expandable basket 514 between the collapsed and expanded configurations. In some instances, the pull wire may be pulled proximally to pull the expandable basket 514, moving the expandable basket 514 to the expanded configuration. In addition, the pull wire may be pushed distally to move the expandable basket 514 into the collapsed configuration. Alternatively, the pull wire may be pushed distally, which may allow the expandable basket 514 to move to the expanded state. In such an instance, the pull wire may be pulled proximally, which may allow the expandable basket 514 to move to the collapsed state.

The modulation system 500 may further include an inner cover or coating (not explicitly shown) disposed on an inner surface of the expandable basket 514. It is contemplated that the inner cover may extend over any length or partial length of the basket 514 desired, or may not even be present. However, this is not required. It is contemplated that in some instances, the inner cover may extend from the proximal end 516 to the distal end 518 of the basket 514.

The modulation system 500 may further include one or more electrode assemblies (not explicitly shown) positioned on an outer surface of the expandable basket 514 and/or inner cover for delivering RF energy to a desired treatment region. The electrode assemblies may be similar in form and function to electrode assemblies 124a, 124b discussed above. However, the modulation systems disclosed herein are not intended to be limited to the use of only flexible circuits to deliver the treatment energy to the treatment region. It is contemplated that the energy delivery devices may be of any type desired. Electrodes 526 on the electrode assemblies may be connected to one another, other electrical components, and/or a power and control unit through one or more electrical conductors 528. The electrodes 526 may be operated in a bi-polar or monopolar mode as desired.

It is contemplated that the modulation system 500 may include any number of electrode assemblies desired based on the size of the modulation device 500 and/or the desired treatment region. For example, the modulation system may include one, two, three, four, five, or more electrode assemblies. It is further contemplated that the electrode assemblies may be staggered about the circumference and/or length of the expandable basket 514 such that a maximum number of electrode assemblies can be positioned on the modulation device.

The modulation system 500 may further include an outer cover or coating 530 disposed on an outer surface of the expandable basket 514 and over the inner cover (when so present). The outer cover 530 may be similar in form and function to outer covers 130, 430 described above. It is contemplated that the outer cover 530 may have a proximal end 531 and a distal end 533. In some instances, the proximal end 531 of the cover 530 may be positioned distal to the proximal end 516 of the basket 514. It is further contemplated that the distal end 533 of the cover 530 may be positioned proximal to the distal end 518 of the basket 514 or may extend to the distal end 518 of the basket 514. This may allow for blood perfusion downstream of the modulation system 500 during treatment. However, it is contemplated that either or both the proximal end 531 or the distal end 533 of the outer cover 530 may extend to the proximal or distal end 516, 518 of the frame 514 as desired. It is contemplated that the inner cover may have a similar configuration to the outer cover 530. The inner and outer covers 530 may be formed of the same material or may be formed from different materials, as desired. In some embodiments, one or both of the inner and/or outer covers 530 may be omitted.

In some instances, the outer cover 530 may be adhered to the inner cover and or basket 514 using methods commonly known in the art. Together, the inner and outer covers 530 may encase all or part of the electrode assemblies and the associated electronics. It is contemplated that the inner and outer covers 530 may fix the electrode assemblies more securely to the expandable basket 514 relative to securing flex circuits to a traditional inflatable balloon as the inner and outer covers 530 sandwich the electrode assemblies and may be more amenable to covalent adhesive bonding. In some instances, the outer cover 530 may not extend over the electrodes 526 of the electrode assemblies. For example, the electrodes 526 may be coated or covered with a masking material prior to application of the outer cover 530. Once the outer cover 530 has been formed, the masking material may be removed to expose the electrodes 530. In some instances, the outer cover 530 may be disposed over the electrodes 530 and subsequently removed, such as, but not limited to laser ablation. This may allow for the electrodes 526 to directly contact the vessel wall. In other instances, the outer cover 530 may remain over the electrodes 526 to allow for insulated wall contact. It is further contemplated that the outer cover 530 may be removed from the electrodes 526 and the electrodes 526 independently coated (for example using parylene) for insulated contact with the desired treatment region.

The materials that can be used for the various components of the modulation systems 100, 300, 400, 500 (and/or other devices disclosed herein) may include those commonly associated with medical devices. For simplicity purposes, the following discussion makes reference to the modulation systems 100, 300, 400, 500. However, this is not intended to limit the devices and methods described herein, as the discussion may be applied to other similar tubular members and/or expandable members and/or components of tubular members and/or expandable members disclosed herein.

The modulation systems 100, 300, 400, 500 and the various components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b- styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions of the modulation systems 100, 300, 400, 500 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the modulation systems 100, 300, 400, 500 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the modulation systems 100, 300, 400, 500 to achieve the same result.

In some embodiments, a degree of Magnetic Resonance Imaging (MRI) compatibility may be imparted into the modulation systems 100, 300, 400, 500. For example, portions of the modulation systems 100, 300, 400, 500 may be made of a material that does not substantially distort the image and create substantial artifacts (i.e., gaps in the image). Certain ferromagnetic materials, for example, may not be suitable because they may create artifacts in an MRI image. In some of these and in other embodiments, portions of the modulation systems 100, 300, 400, 500 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An intravascular nerve modulation system, comprising:
    an outer elongate shaft having a proximal end, a distal end, and a lumen extending therebetween;
    an inner elongate shaft having a proximal end and a distal end;
    an expandable basket having a proximal end and a distal end, the proximal end of the expandable basket affixed adjacent to the distal end of the outer elongate shaft;
    an electrode assembly that comprises a flexible circuit comprising one or more electrodes affixed adjacent to the expandable basket;
    an inner cover disposed over an inner surface of the expandable basket; and
    an outer cover disposed over the outer surface of the expandable basket;
    wherein the flexible circuit is disposed between the inner cover and the outer cover; and
    wherein the system does not comprise an inflation lumen.

2. The nerve modulation system of claim 1, wherein the electrode assembly is affixed to a surface of the inner cover.

3. The nerve modulation system of claim 1, wherein the electrode assembly is affixed to an outer surface of the expandable basket.

4. The nerve modulation system of claim 1, wherein the electrode assembly is affixed to an inner surface of the outer cover.

5. The nerve modulation system of claim 1, further comprising one or more additional electrode assemblies.

6. The nerve modulation system of claim 5, wherein the electrode assembly and the one or more additional electrode assemblies are spaced about a circumference of the expandable basket.

7. The nerve modulations system of claim 1, wherein the outer cover and the inner cover comprise an elastomeric material.

8. The nerve modulation system of claim 7, wherein the outer cover and the inner cover comprise the same elastomeric material.

9. The nerve modulation system of claim 7, wherein the outer cover and the inner cover comprise different elastomeric materials.

10. An intravascular nerve modulation system, comprising:
    an outer elongate shaft having a proximal end, a distal end, and a lumen extending therebetween;
    an inner elongate shaft having a proximal end and a distal end;
    an expandable basket having a proximal end and a distal end, the proximal end of the expandable basket affixed adjacent to the distal end of the outer elongate shaft and the distal end of the expandable basket affixed adjacent to the distal end of the inner elongate shaft;
    an electrode assembly that comprises a flexible circuit comprising one or more electrodes affixed to an outer surface of the expandable basket;
    an outer cover disposed over the outer surface of the expandable basket and at least a portion of the electrode assembly; and
    an inner cover disposed over an inner surface of the expandable basket;
    wherein the expandable basket has a collapsed configuration and an expanded configuration;
    wherein the flexible circuit is disposed between the inner cover and the outer cover; and
    wherein the system does not comprise an inflation lumen.

11. The nerve modulation system of claim 10, wherein in the expanded configuration, the distal end of the expandable basket and the proximal end of the expandable basket have a tapered cross-sectional area.

12. The nerve modulation system of claim 10, further comprising one or more additional electrode assemblies.

13. The nerve modulation system of claim 12, wherein the electrode assembly and the one or more additional electrode assemblies are spaced about a circumference of the expandable basket.

14. The nerve modulation system of claim 10, wherein the outer cover and the inner cover comprise an elastomeric material.

15. An intravascular nerve modulation system, comprising:
    an outer elongate shaft having a proximal end, a distal end, and a lumen extending therebetween;
    an inner elongate shaft having a proximal end and a distal end;
    an expandable basket having a proximal end and a distal end, the proximal end of the expandable basket affixed adjacent to the distal end of the outer elongate shaft;
    an electrode assembly that comprises a flexible circuit comprising one or more electrodes affixed to an outer surface of the expandable basket; and
    an outer cover disposed over the outer surface of the expandable basket and at least a portion of the electrode assembly;
    an inner cover disposed over an inner surface of the expandable basket;
    wherein the expandable basket is capable of actuating between a collapsed configuration and an expanded configuration and in the expanded configuration the distal end of the expandable basket has a larger cross-sectional area than the proximal end of the expandable basket;
    wherein the flexible circuit is disposed between the inner cover and the outer cover; and
    wherein the system does not comprise an inflation lumen.

16. The intravascular nerve modulation system of claim 1, wherein the outer cover extends over the electrodes of the electrode assemblies and the electrodes are configured for insulated contact with a surrounding treatment region.

17. The intravascular nerve modulation system of claim 1, wherein the outer cover does not extend over the electrodes of the electrode assemblies.

18. The intravascular nerve modulation system of claim 1, wherein openings are provided in the outer cover, at the proximal and distal ends of the basket such that blood is allowed to perfuse downstream of the system while the basket is in an expanded configuration in a blood vessel of a subject.

19. The intravascular nerve modulation system of claim 18, wherein openings are provided in the inner cover.

20. The intravascular nerve modulation system of claim 1, wherein the electrodes of the electrode assemblies are covered and configured for insulated contact with a surrounding treatment region.

* * * * *